US005641671A

United States Patent [19]
Bos et al.

[11] Patent Number: 5,641,671
[45] Date of Patent: Jun. 24, 1997

[54] **PRODUCTION OF ACTIVE *PSEUDOMONAS GLUMAE* LIPASE IN HOMOLOGOUS OR HETEROLOGOUS HOSTS**

[75] Inventors: Jannetje Wilhelmina Bos, Capelle a/d IJssel; Leon Gerardus Frenken, Rotterdam; Cornelis Theodorus Verrips, Maassluis; Christiaan Visser, Capelle a/d IJssel, all of Netherlands

[73] Assignee: Unilever Patent Holdings B.V., Rotterdam, Netherlands

[21] Appl. No.: 34,650

[22] Filed: Mar. 22, 1993

Related U.S. Application Data

[63] Continuation of Ser. No. 727,235, Jul. 3, 1991, abandoned.

[30] Foreign Application Priority Data

| Jul. 6, 1990 | [EP] | European Pat. Off. ............ 90307440 |
| Jul. 9, 1990 | [WO] | WIPO ...................... PCT/EP90/01138 |
| Oct. 17, 1990 | [EP] | European Pat. Off. ............ 90202772 |

[51] Int. Cl.[6] .................. C12N 1/20; C12N 1/15; C12N 1/19; C12N 15/55
[52] U.S. Cl. ............... 435/198; 435/252.31; 435/252.33; 435/252.34; 435/254.2; 435/254.21; 435/254.23; 536/23.2
[58] Field of Search .................. 435/172.3, 198, 435/254.2, 254.3, 254.23, 252.3, 252.31, 252.33, 252.34, 254.21; 536/23.2

[56] References Cited

U.S. PATENT DOCUMENTS

| 4,508,827 | 4/1985 | Olsen ................... 435/252.34 |
| 4,551,433 | 11/1985 | De Boer ................... 435/252.33 |
| 4,897,471 | 1/1990 | Stabinsky ................... 536/23.1 |

FOREIGN PATENT DOCUMENTS

| 0206390 | 12/1986 | European Pat. Off. . |
| 0318775 | 6/1989 | European Pat. Off. . |
| 0331376 | 9/1989 | European Pat. Off. . |
| 0407225 | 1/1991 | European Pat. Off. . |
| 3908131 | 10/1989 | Germany ............ C07K 15/04 |
| 9100908 | 1/1991 | WIPO . |

OTHER PUBLICATIONS

Jorgensen et al., "Cloning, Sequence & Expression of a Lipase Gene from *Pseudomonas cepacia*: Lipase Production in Heterologous Hosts Requires Two Pseudomonas Genes", Journal of Bacteriology vol. 173 No. 2, Jan. 1991, pp. 559–567.

Biotechnology Abstracts Database abstract No. 89–02896, 1989, Derwent Pub. Ltd., London, GB; Aoyama et al.: "Cloning, sequencing and expression of the lipase gene from Pseudomonas fragi IFO–12049 in *E. coli*", vol. 242, pp. 36–40.

Chihari–Siomi et al, Arch. of Biochem. & Biophys., vol. 296, No. 2, pp. 505–513 (1992).

Reznikoff, in Maximizing Gene Expression, Butterworth Publishers, Stoneham, MA, pp. 1–4 (1986).

*Primary Examiner*—Mindy B. Fleisher
*Assistant Examiner*—Nancy T. Vogel
*Attorney, Agent, or Firm*—Cushman Darby & Cushman, L.L.P.

[57] ABSTRACT

The production of an active *Pseudomonas glumae* lipase isolated from *P. glumae* PG1 (CBS 322.89) and other lipases suitable for application in detergent systems is described in homologous, but particularly in heterologous hosts, e.g. *Bacillus subtilis*. For the latter a "helper function" or "lipase-specific stabilization/translocation protein" is needed, for which a gene is provided which, when expressed in concert with the lipase gene, can improve the stabilization of the intermediates involved in the production and translocation/secretion of the lipase. The hosts are transformed by recombinant DNA methods and modified lipases can be made by site-directed mutation or classical mutation techniques. The lipase gene and the gene encoding the helper function can be part of one operon that can be transcribed to form a polycistronic messenger or be present as separate genes yielding two mRNA's on transcription. The production level can be further improved by optimizing the regulation sequences. It can be advantageous to use at least part of the signal sequence of the lipase gene in addition to a signal sequence homologous to the host in which the lipase is produced.

10 Claims, 27 Drawing Sheets

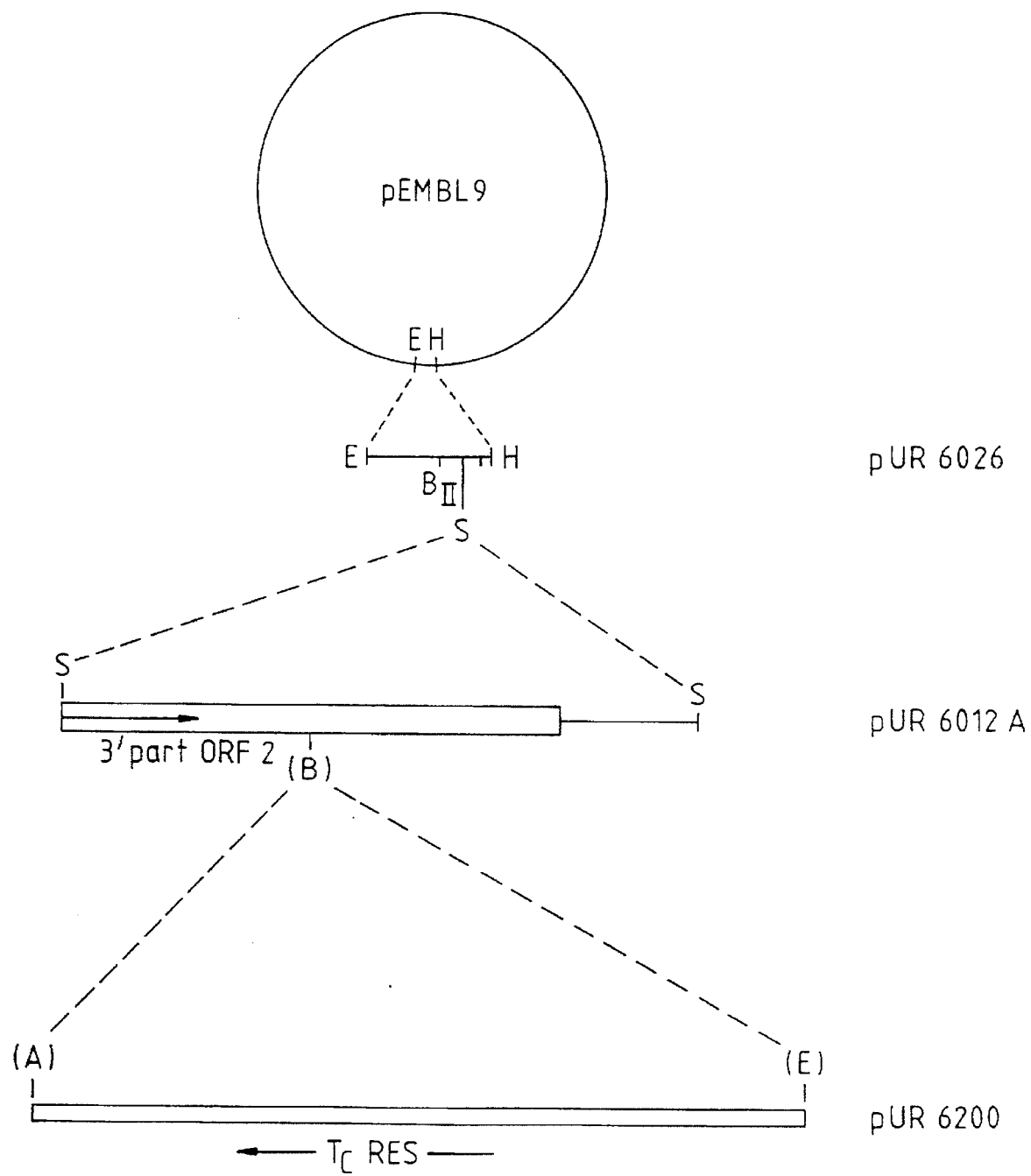

Fig. 2A

```
       BamHI
 1   ----+----|----+----|----+----|----+----|----+----|----+----|   60
     GGATCCTGCCTTGAGCCGGGGGCCGGGTCCGGAGCCCGCCTTCCGGGTTCATCCCGACCCGT

EcoRI
 61  ----+----|----+----|----+----|----+----|----+----|----+----|  120
     TCTGAATTCACCTTGAACGCAGGCGTTTCGCGGGCCTTCGCGCTGCGGCCGCAAT

121  ----+----|----+----|----+----|----+----|----+----|----+----|  180
     ACGTCTCGCGCCGTGTCATGTCGGATGCAATCGTCGGCAATCGGCGTGATTGTT

181  ----+----|----+----|----+----|----+----|----+----|----+----|  240
     GCGCCCGCAACCTGATCGCCCCGCGTGGCGGGCACGGCCATTCACC

ClaI
241  ----+----|----+----|----+----|----+----|----+----|----+----|  300
     GGATCGATCGCGCCGCGCCTTGCGCCGCAGCATCCGCGCCGTCATATGTCCACCCGCCGC
```

Fig.2B

```
301 ---------+---------+---------+---------+---------+---------+ 360
    GCGGGGCGCTGTCCATCGAGTAGAGACGGCCTATCCAAACGGCCGTCTGATTGCAGACAGG

361 ---------+---------+---------+---------+---------+---------+ 420
    AGCCGGCCGCCCGGCCATGTTTCACTCCGACTTGCCGCTCGAGCGTGCCGACGACCTGAGAA

421 ---------+---------+---------+---------+---------+---------+ 480
    CGGCGGCCGCCCGCCCGGCCGTGGCATTCCGGATCGACGTAACCGATAACGATGGAGATAA
                                              ClaI
481 ---------+---------+---------+---------+---------+---------+ 540
    ACATGGTCAGATCGATGCCGTTCCAGGTGCGGCGGGCGGAGGCGGTGGCATGGGCGTTGGCGG
     MetValArgSerMetArgSerArgValAlaAlaArgAlaValAlaAlaTrpAlaValAlaV

541 ---------+---------+---------+---------+---------+---------+ 600
    TGATGCCGCTGCCGGCGCCGGGGTTGACGATGGCCGCTCGCCCGGCCGTCGCCCGGCCTCGCGG
    alMetProLeuAlaGlyAlaAlaGlyLeuThrMetAlaAlaSerProAlaAlaValAlaA
                                                              -1 ↑
```

Fig. 2C

```
601 CGGACACCTACGGGCGACGGCTATCCGGTGATCCTCGTCCACGGCCTCGGGCCACCG   660
    ----+----+----+----+----+----+----+----+----+----+----+
     laAspThrTyrAlaAlaThrArgTyrProValIleLeuValHisGlyLeuAlaGlyThrA
     +1

661 ACAAGTTCGCGAACGTGGTCGACTATTGGTACGGAATCCAGAGCGATCTCCAATCGCATG   720
    ----+----+----+----+----+----+----+----+----+----+----+
     spLysPheAlaAsnValValAspTyrTrpTyrGlyIleGlnSerAspLeuGlnSerHisG

721 GCGGAAGGTGTACGTCGCGAATCTCTCGGATTCCAGAGCGACGACGGGCCGAACGGCC   780
    ----+----+----+----+----+----+----+----+----+----+----+
                       PvuII
     lyAlaLysValTyrValAlaAsnLeuSerGlyPheGlnSerAspAspGlyProAsnGlyA

781 GCGGCGAGCAGCTGCTCGCCTACGTGAAGCAGGTGCTCGCGGCAGCCACCGGCGACCAAGG   840
    ----+----+----+----+----+----+----+----+----+----+----+
     rgGlyGluGlnLeuLeuAlaTyrValLysGlnValLeuAlaAlaThrGlyAlaThrLysV

841 TGAACCTGATCGGCCACAGCCAGGGCGGCCTGACCTCGCGCTACGTCGCGGCCGTCGCGC   900
    ----+----+----+----+----+----+----+----+----+----+----+
     alAsnLeuIleGlyHisSerGlnGlyGlyLeuThrSerArgTyrValAlaAlaValAlaP
```

Fig. 2D

```
901       ---------+---------+---------+---------+---------+---------+   960
          CGCAACTGGTGGCCTCGGTGACGACGATCGGCACGCCCATCGGCACGCCGCTCCGAGTTCGCCG
          roGlnLeuValAlaSerValThrThrIleGlyThrProHisArgGlySerGluPheAlaA

SalI
961       ---------+---------+---------+---------+---------+---------+  1020
          ACTTCGTGCAGGACGTGCTGAAGACCGATCCGACCGGGCTCTCGTCGACGGTGATCGCCG
          spPheValGlnAspValLeuLysThrAspProThrGlyLeuSerSerThrValIleAlaA

1021      ---------+---------+---------+---------+---------+---------+  1080
          CCTTCGTCAACGTGTTCGGCACGCTCGTCAGCAGCTCGCACAACACCGACCAGGACGCC
          laPheValAsnValPheGlyThrLeuValSerSerSerHisAsnThrAspGlnAspAlaL

1081      ---------+---------+---------+---------+---------+---------+  1140
          TCGCGGGCGCTGCGCACGCTCACCACCGCCAGACCGCCACCTACAACCGGAACTTCCCGA
          euAlaAlaLeuArgThrLeuThrThrAlaGlnThrAlaThrTyrAsnArgAsnPheProS

1141      ---------+---------+---------+---------+---------+---------+  1200
          GCGCGGGCCTGGGGCCCGGTTCGTGCCAGACGGGCCGACCGAAACCGGTCGGCG
          erAlaGlyLeuGlyAlaProGlySerCysGlnThrGlyAlaAlaThrGluThrValGlyG
```

Fig. 2E

```
1201                                                     1260
     GCAGCCAGCACCTGCTCTATTCGTGGGGGGCACCGGGATCCAGCCCACCTCCACCGTGC
     lySerGlnHisLeuLeuTyrSerTrpGlyGlyThrAlaIleGlnProThrSerThrValL 1261                                                     1320
     TCGGGCGTGACCGGCGGCGACCGACACCAGCACGCTCGACGTCGCGAACGTGACCG
     euGlyValThrGlyGlyAspThrThrSerThrLeuAspValAlaAsnValThrA 1321                                                     1380
     ACCCGTCCAGCTCCACGCTCGCCGTGCTGGCCACCGGCGGTGATGATCAATCGCGGGGC
     spProSerThrLeuAlaLeuAlaThrGlyAlaValMetIleAsnArgAlaSerGlyG
                                                 PstI 1381                                                     1440
     AGAACGACGGCTCGTCTCGCGCTCGCCTGCAGCTCGTGTTCGGGCAGGTGATCAGCACCAGCT
     lnAsnAspGlyLeuValSerArgCysSerSerLeuPheGlyGlnValIleSerThrSerT
                                                 PvuII 1441                                                     1500
     ACCACTGGAACCATCTCGACGAGATCAACCAGCTGCTCGGCGTGCGGCGCCAACGCGG
     yrHisTrpAsnHisLeuAspGluIleAsnGlnLeuLeuGlyValArgGlyAlaAsnAlaG
```

Fig. 2F

```
                                                                              PstI
1501  ----------+---------+---------+---------+---------+---------+  1560
      AAGATCCGGTCGCGGGTGATCCGGCACGCGAACCGGCTCAAGCTGCAGGGCGTGTGAT
      luAspProValAlaValIleArgThrHisValAsnArgLeuLysLeuGlnGlyValEnd

1561  ----------+---------+---------+---------+---------+---------+  1620
      GGGCGCAGGCCGATCGTCCGGCGGGCTGCCGGGCCCGATGCGGCGGGCGTC
                                                    SacII
1621  ----------+---------+---------+---------+---------+---------+  1680
      GTTCGGCGGCTGGCCGGGCCTCTGTGCCGGTCGTGTGGCTTCG

1681  ----------+---------+---------+---------+---------+---------+  1740
      GCCCGCCGCCCGTCGCGCCGGCTCGCGGGGCCGGCCGGCGT

SacII
1741  ----------+---------+---------+---------+---------+---------+  1800
      GCCCGCCGGCAAGCGGCGGGAGGCCCATGCCGTTGCCGGGCTGCCGGG
```

Fig. 2G

```
                                                              NruI
       ----------+---------+---------+---------+---------+---------+  1860
1801   CGGCTGGCTGGCTCGGCATGCCGGCCCGGCTGGCCGCCCGGCGGGGCCGGCTCGCGAG

----------+---------+---------+---------+---------+---------+  1920
1861   GACGCGGCGGTGCCGGAGTTCTTCGACTATGCCTGACCGCGCAGGGCGAACTGACGCC

----------+---------+---------+---------+---------+---------+  1980
1921   CGGCCGGCCTCGATGCGCTGGGTGCGCGAGATCGCCGAGCTTGACGGCAGCCCCGC

----------+---------+---------+---------+---------+---------+  2040
1981   GCAAGCGGAGGCGCTCGGGCCGTCTTGGCCGCTATCGCGCCTACTTCGACGGCTCGGCA

----------+---------+---------+---------+---------+---------+  2100
2041   ATTGCCCGGCGACGGCGGGTGCTCGGGGACAAGCTCGATCCGGCCATGCAGCTCGC
```

Fig. 2H

```
2101 ----+----+----+----+----+----+ 2160
     GCTCGATCAGCGGCGGGCGCTGGCCGACCCGCACGCTCGGCCGAGTGGGCCGAGCCGTTCTT

BamHI
2161 ----+----+----+----+----+----+ 2220
     CGGCGAGGAGCAGCGCCGGCAGCGCCATGACCTCGAACGGATCCGGATCGCCAACGACAC

2221 ----+----+----+----+----+----+ 2280
     CACGCTGAGCCCTGAGCAGAAGGCCGGGCGCTTGCCGCTCGACGGCAGCTGACGCC

2281 ----+----+----+----+----+----+ 2340
     GGACGAGCGGCGCAGCAGGGCGCTGCATGCCGCAGCAGGACGCGGTGACGAAGATCGC

2341 ----+----+----+----+----+----+ 2400
     CGACTTGCAGAAGGCCCGGCCGACCAGATGCCGGCCAGATCGCGGCAGAGCGCT
```

Fig. 2I

```
2401 ----------+---------+---------+---------+---------+---------+ 2460
     CGGGCCCGAGGGCCCGGCCCGCCGAGATGCCAGCAGGACGACGAGGGTGGCAGAC

2461 ----------+---------+---------+---------+---------+---------+ 2520
     GCGCTATCAAGCCTATGCGGCCCGAGCCCGGATCCGGGCCAGGGGCTCGCCCGCA
                                                  NruI
2521 ----------+---------+---------+---------+---------+---------+ 2580
     GGATCGCGGATGCGCGGATCGCGCAGCTCAGGCAGCAGACTTTCACGGCCGGGGAGGC

2581 ----------+---------+---------+---------+---------+---------+ 2640
     GATCCGCGGCGTCGCTCGATCGCGGCGGGGGTTAGGGGCGCCGGCGTGCCGGGC
```

Fig.2J

```
2641 ------+---------+---------+---------+---------+---------+ 2700
      ACCGTGTGCTTCGGAGTGCTTCGAACGGGTGGGCCGCACGGGCGTTCCAGCCGGCTGCA

2701 ------+---------+---------+---------+---------+---------+ 2760
      TCGCGTGTTTCGTACTGAAATGGCATGAGTGACAGCGTGCCGACAGCGTGCTGACAGGT

2761 ------+---------+---------+---------+---------+---------+ 2820
      TCCCGGTTTTTGCCTTTCCACGTGCTTTCATTGGGCCGGAGCGAGCAAGAATCACGAC

ClaI
2821 ------+---------+---------+---------+---------+---------+ 2880
      GCTCTGCAACAATGGGGCGGATGGGCGGTTTGACGGTCGGAATCGATGCAAACGGCCG

SacII
2881 ------+--------+ 2900
      CCGGCGTCGTTCCATCCGCGG
```

Fig. 3.

MetAlaGlnAlaAspArgProAlaArgGlyGlyLeuAlaAlaArgProMetArgGlyAla-
SerPheAlaLeuAlaGlyLeuValAlaCysAlaAlaCysAlaAlaValValLeuTrpLeu-
ArgProAlaAlaProSerProAlaProAlaGlyAlaValAlaGlyGlyProAlaAlaGly-
ValProAlaAlaAlaSerGlyAlaAlaGluAlaAlaMetProLeuProAlaAlaLeuPro-
GlyAlaLeuAlaGlySerHisAlaProArgLeuProLeuAlaAlaGlyGlyArgLeuAla-
ArgThrArgAlaValArgGluPhePheAspTyrCysLeuThrAlaGlnGlyGluLeuThr-
ProAlaAlaLeuAspAlaLeuValArgArgGluIleAlaAlaGlnLeuAspGlySerPro-
AlaGlnAlaGluAlaLeuGlyValTrpArgArgTyrArgAlaTyrPheAspAlaLeuAla-
GlnLeuProGlyAspGlyAlaValLeuGlyAspLysLeuAspProAlaAlaMetGlnLeu-
AlaLeuAspGlnArgAlaAlaLeuAlaAspArgThrLeuGlyGluTrpAlaGluProPhe-
PheGlyAspGluGlnArgArgGlnArgHisAspLeuGluArgIleArgIleAlaAsnAsp-
ThrThrLeuSerProGluGlnLysAlaAlaArgLeuAlaAlaLeuAspAlaGlnLeuThr-
ProAspGluArgAlaGlnGlnAlaAlaLeuHisAlaGlnGlnAspAlaValThrLysIle-
AlaAspLeuGlnLysAlaGlyAlaThrProAspGlnMetArgAlaGlnIleAlaGlnThr-
LeuGlyProGluAlaAlaAlaArgAlaAlaGlnMetGlnGlnAspAspGluAlaTrpGln-
ThrArgTyrGlnAlaTyrAlaAlaGluArgAspArgIleAlaAlaGlnGlyLeuAlaPro-
GlnAspArgAspAlaArgIleAlaGlnLeuArgGlnGlnThrPheThrAlaProGlyGlu-
AlaIleArgAlaAlaSerLeuAspArgGlyAlaGlyGly

E. coli growth experiment induction with IPTG

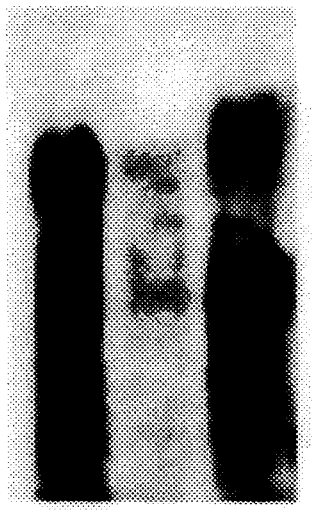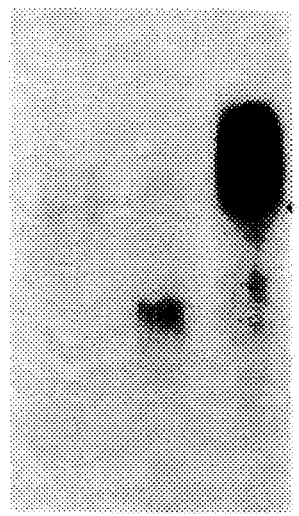
Fig. IIA    Fig. IIB

Fig. 15A

```
     PstI                                                          PvuI
  1  CTGCAGGGCGTGTGATGGCGCAGGCCGATCGTCCTGCAAGAGGAGGCCTGGCTGCAAGAC   60
     ----+----|----+----|----+----|----+----|----+----|----+----|
     GACGTCCCGCACACTACCGCGTCCGGCTAGCAGGACGTTCTCCTCCGGACCGACGTTCTG

61  CTATGAGAGGCGCATCTTTCGCTGGCAGGTCTGGTCGCCAGTCTTGTGCAGCCG        120
     ----+----|----+----|----+----|----+----|----+----|----+----|
     GATACTCTCCGCGTAGAAAGCGACCGTCCAGACCAGCGGTCAGAACACGTCGGC

121  TAGTACTGTGGCTGAGACCACCTTCTCCTGCTCCAGCGGCACAGTTGCAGGCG         180
     ----+----|----+----|----+----|----+----|----+----|----+----|
     ATCATGACACCGACTCTGGTGGAAGAGGACGAGTCGCCGTGTCAACGTCCGC

181  GACCTGCCGCGGGAGTTCCAGCGCAGCATCTGGGCGCAGCTGAAGCAGCCGATGCCTTTAC  240
     ----+----|----+----|----+----|----+----|----+----|----+----|
     CTGGACGGCGCCCTCAAGGTCGCGTCGTAGACCCGCGTCGACTTCGTCGCTACGGAAAT

241  CTGCTGCATTGCCTGGCGCACTTGCCGGATCGCCAAGACTGCCGCTTGCGGCAG        300
     ----+----|----+----|----+----|----+----|----+----|----+----|
     GACGACGTAACGGACCGCGTGAACGGCCTAGCGGTTCTGACGGCGAACGCCGTC
```

Fig. 15B

```
     GTGGACGCTTGGCACGCGCACAAGAGCCGTCAGAGAGTTCTTTGATTATTGCCTTACTGCGC
301  ----------+----------+----------+----------+----------+----------+  360
     CACCTGCGAACCGTGCGTGTTCTCGGCAGTCTCTCAAGAAACTAATAACGGAATGACGCG

AGGGCGAATTGACGCGCCTGCTGCCCTGGACGCACTGTGGTTAGACGGAAATTGCAGCGCAAC
361  ----------+----------+----------+----------+----------+----------+  420
     TCCCGCTTAACTGCGCGGACGACGGGACCTGCGTGACCAATCTGCGCTTTAACGTCGCGTTG

TTGATGGATCTCCAGCTCAAGCAGAAGCTCTTGGCGTCTGGCGTAGATATCGCGCGTACT
421  ----------+----------+----------+----------+----------+----------+  480
     AACTACCTAGAGGTCGAGTTCGTCTTCGAGAACCGCAGACCGCATCTATAGCGCGCATGA

TTGATGCATTGGCCCAGCTTCCTGGCGACGGAGCGGTTCTTGGTGATAAATTAGATCCTG
481  ----------+----------+----------+----------+----------+----------+  540
     AACTACGTAACCGGGTCGAAGGACCGCTGCCTCCGCCAAGAACCACTATTTAATCTAGGAC

CCGCTATGCAACTGGCACTTGATCAACGTGCAGCGTTGGCCCGACCGCACGCTTGGCGAGT
541  ----------+----------+----------+----------+----------+----------+  600
     GGCGATACGTTGACCGTGAACTAGTTGCACGTCGCAACGGCTGGCGTGCGAACCGCTCA

BamHI
     GGGCTGAACCATTCTTCTTGGGCGACGAGCAGAAGACAACGCCATGATCTTGAAAGGATCC
601  ----------+----------+----------+----------+----------+----------+  660
     CCCGACTTGGTAAGAAGAACCCGCTGCTCGTCGTCTTCTTGTTGCGGTACTAGAACTTTCCTAGG
```

Fig. 16A

```
     EcoRI
     GAATTCATGGGCGCAGGCCGATCGTCCTGCAAGAGGAGCCTGGCTGCAAGACCTATGAGA
  1  ------+---------+---------+---------+---------+---------+   60
     CTTAAGTACCCGCGTCCGGCTAGCAGGACGTTCTCCTCCGGACCGACGTTCTGGATACTCT

GGGCGCATCTCTTCGCGCTGGCAGGTCTGGTCGCGTGTGCAGCTTGTGCAGCCGTAGTACTG
 61  ------+---------+---------+---------+---------+---------+  120
     CCGCGTAGAAAGCGCGACCGTCCAGACCAGCGCACACGTCGAACACGTCGGCATCATGAC

TGGCTGAGACCAGCGGGCACCCTTCTCCCTGCTCCAGCAGGCGCAGTTGCAGGCGGACCTGCC
121  ------+---------+---------+---------+---------+---------+  180
     ACCGACTCTGGTCGCCCGTGGGAAGAGGACGAGTCGTCCGCGTCAACGTCCGCCTGGACGG

GCGGGAGTTCCAGCGGCAGCATCTGGCGCCAGCTGAAGCAGCGATGCCTTTACCTGCTGCA
181  ------+---------+---------+---------+---------+---------+  240
     CGCCCTCAAGGTCGCCGTCGTAGACCGCGGTCGACTTCGTCGCTACGGAAATGGACGACGT

TTGCCCTGGCGCACTTGCCGGATCGCATGCCCAAGACTGCGCGCTTGCGGCAGGTGGACGC
241  ------+---------+---------+---------+---------+---------+  300
     AACGGACCGCGTGAACGGCCCTAGCGTACGCGGTTCTGACGCGCGAACGCCGTCCACCTGCG
```

Fig. 16B

```
301  TTGGCACGCACAAGAGCCGTCAGAGAGTTCTTTGATTATTGCCTTACTGCGCAGGGCGAA
     ----+----+----+----+----+----+----+----+----+----+----+----+   360
     AACCGTGCGTGTTCTCGGCAGTCTCTCAAGAAACTAATAACGGAATGACGCGTCCCGCTT

361  TTTGACGCCTGCTGCCCTGGACGCCACTGGTTAGACCGGAAATTGCAGCGCAACTTGATGGA
     ----+----+----+----+----+----+----+----+----+----+----+----+   420
     AACTGCGGACGACGGGACCTGCGGTGACCAATCTGGCCTTTAACGTCGCGTTGAACTACCT

421  TCTCCAGCTCAAGCAGAAGCTCTTGGCGTCTGGCCGTAGATATCGGCGTACTTTGATGCA
     ----+----+----+----+----+----+----+----+----+----+----+----+   480
     AGAGGTCGAGTTCGTCTTCGAGAACCGCAGACCGGCATCTATAGCCGCATGAAACTACGT

481  TTGGCCCAGCTTCCTGGCGACGGAGCGGTTCTTGGTGATAAATTAGATCCTGCCGCTATG
     ----+----+----+----+----+----+----+----+----+----+----+----+   540
     AACCGGGTCGAAGGACCGCTGCCTCGCCAAGAACCACTATTTAATCTAGGACGGCGATAC

541  CAACTGGCACTTGATCAACGTGCCAGCGTTGGCCGACCGGTTGGCGTGCGAGTGGGCTGAA
     ----+----+----+----+----+----+----+----+----+----+----+----+   600
     GTTGACCGTGAACTAGTTGCACGGTCGCAACCGGCTGGCCAACCGGCGAACCGCTCACCCGACTT

BamHI
601  CCATTCTTTGGCGACGAGCAGAGAAGACAACGCCATGATCTTGAAAGGATCC
     ----+----+----+----+----+----+----+----+----+----+--   652
     GGTAAGAAACCGCTGCTCGTCTCTTCTGTTGCGGTACTAGAACTTTCCTAGG
```

PRODUCTION OF ACTIVE *PSEUDOMONAS GLUMAE* LIPASE IN HOMOLOGOUS OR HETEROLOGOUS HOSTS

This is a continuation of application Ser. No. 07/727,235, filed on Jul. 3, 1991, now abandoned.

TECHNICAL FIELD

The invention relates to the production of lipases suitable for application in detergent and cleaning compositions. In particular, the invention relates to the efficient production of lipases in homologous or heterologous hosts. More in particular, the invention relates to the production by various hosts of a *Pseudomonas glumae* lipase isolated from *P. glumae* PG1, deposited at the Centraalbureau voor Schimmelcultures at Baarn, The Netherlands, on Jul. 6, 1989, as CBS 322.89. In this specification the abbreviated form P. is also used instead of the full term Pseudomonas.

For the lipase originating from *P. glumae* PG1 in this specification a *Pseudomonas glumae* (alias *Pseudomonas gladioli*) as well as closely related Pseudomonas species, like *Pseudomonas cepacia* and *P. solanacearum*, are considered as homologous hosts. Most of these bacteria are mentioned in our copending, not pre-published patent applications EP-A-407 225 and WO-A-91/00920, which are incorporated herein by reference. All other microorganisms can be considered as heterologous hosts, which can be Gram negative or Gram positive bacteria, as well as lower eukaryotes.

BACKGROUND AND PRIOR ART

Many proteins which are excreted by prokaryotes, are translocated across the cytoplasmic membrane in a signal-peptide dependent way. The proteins are produced intracellularly as precursor molecules having an N-terminal extension of 20 to 40 amino acids, the pre-sequence or signal sequence. After or during the translocation of the protein this sequence is cleaved off by a highly specific signal peptidase. Although there is little homology between the amino acid sequence of the signal sequences, they share a common architecture (von Heijne, 1985). The three characteristic parts are: a positively charged (n)-region, a hydrophobic (h)-region and a (c)-region consisting mainly of small neutral residues and comprising the proteolytic cleavage site (Gierasch, 1989). Some signal sequences are much longer and can be considered as a pre-pro signal sequence, e.g. for subtilisin, whereby the pre-sequence has a function similar to that in normal signal sequences but the pro-sequence is related to control the enzymic activity and has to be hydrolysed before the enzyme become active (Zhu, 1989).

Besides this signal sequence an export apparatus, comprising cytoplasmic and membrane associated components, is involved in the translocation of the proteins. For *Escherichia coli* a set of proteins required for protein translocation have been identified, several of which have been cloned and characterized: SecA(PrlD) (Schmidt, 1988; Akita, 1990), SecB (Kumamoto, 1989), SecD (Gardel, 1987), SecE(PrlG) (Schatz, 1989), SecY(PrlA) (Cerretti, 1983; Bieker, 1990), GroEL (Laminet, 1990), trigger factor (Crooke, 1988). Some of these proteins (SecB, GroEL, trigger factor) are located in the cytoplasm and function as "molecular chaperons" in order to maintain the precursor molecules in a translocation competent state (Lecker, 1989). The 16 kd SecB protein forms tetrameric complexes and is believed to be a cytosolic signal recognition factor (Watanabe, 1989; Lecker, 1990). GroEL forms a ring shaped oligomer made up of 14 identical 65 kd subunits. Together with GroES and in the presence of hydrolysable $Mg^{2+}$-ATP it forms GroE complexes which are essential for growth and are also involved in the heat-shock response (Laminet, 1990). The trigger factor is a 63 kd protein which binds to the ribosomal 50S subunit and interacts with precursor proteins and the cytoplasmic membrane (Crooke, 1988; Lill, 1988). The secA gene product is a large (102 kd) inner-membrane associated protein with ATPase activity (Lill, 1989). SecY (68 kd) and SecE (13,6 kd) are integral membrane proteins who have been shown to interact while mediating translocation (Bieker, 1990).

Recently a SecY homologue has been isolated from *Bacillus subtilis* (Suh, 1990; Nakamura, 1990), suggesting similarities between the export apparatus of Gram negative and Gram positive bacteria. In the case of Gram positive bacteria translocation across the cytoplasmic membrane means excretion into the culture-medium. For Gram negative bacteria, however, a second membrane has to be traversed before a protein can be released into the culture medium. Translocation of proteins across the outer membrane of Gram negative bacteria is more or less specific for a given protein or group of proteins for which specific helper proteins are required. Examples are protease of *Xanthomonas campestris* pathovar *campestris* (Liu, 1990). In some cases it was possible to transfer the structural gene as well as the helper genes into *E. coli* and get functional expression and excretion into the medium (d'Enfert, 1987; Schiebel, 1989). In some cases no additional translocation proteins are required. Two examples are the IgA protease of *Neisseria gonorrhoeae* (Pohlner, 1987) and the serine protease of *Serratia marcescens* (Yanagida, 1986; Miyazaki, 1989). Both enzymes are produced as prepro-enzymes having an N-terminal signal sequence guiding the precursors through the cytoplasmic membrane, and a C-terminal peptide responsible for the translocation across the outer membrane. Both enzymes could be produced and excreted by *E. coli* without the expression of specific helper genes from these bacteria being necessary.

In our copending EP-A-407 225 it is disclosed that on growing the heterologous Gram negative host *Pseudomonas putida* WCS358 transformed with pUR6502 or pUR6522 on BYPO plates with and without IPTG a surprising result was found. It appeared that *P. putida* WCS358 transformed by introducing pUR6522 (containing an expressible combination of the lipA gene and a downstream fragment of at least 1.5 kb, preceded by the tac promoter) produced significant amounts of lipase (demonstrated by the large halo formation), whereas the strain containing pUR6502 (comprising the lipA gene and a downstream fragment of less than about 700 bp, preceded by the tac promoter) produced hardly any lipase. This finding suggested the presence of a specific "helper-function" for lipase, encoded by the 3'-region of the lipase gene extending beyond the BamHI site.

It is an object of the present invention to provide an improved process for the production of lipase by means of a microorganism. It is a further object of the present invention to provide an improved production of lipase in *Pseudomonas glumae* by optimizing the original promoter significantly by classical or site-directed mutagenesis techniques.

It has now been found that the pre-lipase gene from *P. glumae* PG1 alone was not always sufficient for obtaining production of active lipase in heterologous hosts. It further appeared that in *P. glumae* PG1 downstream of this lipase gene another gene is present which is involved in a proper and/or optimal production of extracellular active lipase, in particular when the lipase gene is expressed in heterologous hosts like *P. putida*. This continued research has revealed that these two genes (i.e. lipase and ORF2) are present in the *Pseudomonas glumae* chromosome in a two-gene operon.

In this specification this helper-function is referred to as the "ORF2 gene product" or the "lipase-specific stabilization/translocation protein". The DNA sequence encoding this protein is indicated as "ORF2" or the "ORF2 gene". It will be understood that folding of a protein is an important factor for both the stabilization and translocation of a protein.

In EP-A-331 376 (AMANO) there is described a "gene participating in the production of lipase" originating from *Pseudomonas cepacia* FERM-12-33 (FERM BP-2293). The DNA sequence of the gene is not given but only the amino acid sequence of the protein which is said to be encoded by the gene. When comparing this amino acid sequence with that of the lipase-specific stabilization/translocation protein originating from the lipase-producing Gram negative bacterium *P. glumae* PG1 given in FIG. 3 of the present specification, it is clear that the proteins differ appreciably. It is unlikely that these different proteins have the same function.

DEFINITION OF THE INVENTION

In its broadest embodiment the present invention provides a transformed microorganism capable of producing a lipase, said microorganism containing at least one expressible lipase gene and at least one expressible gene encoding a lipase-specific stabilization/translocation protein, either one or both of these genes originating from a lipase-producing Gram negative bacterium. Moreover, the invention provides a process for producing a lipase by means of a transformed microorganism according to the invention.

DETAILED DESCRIPTION OF THE INVENTION

Figure 4:
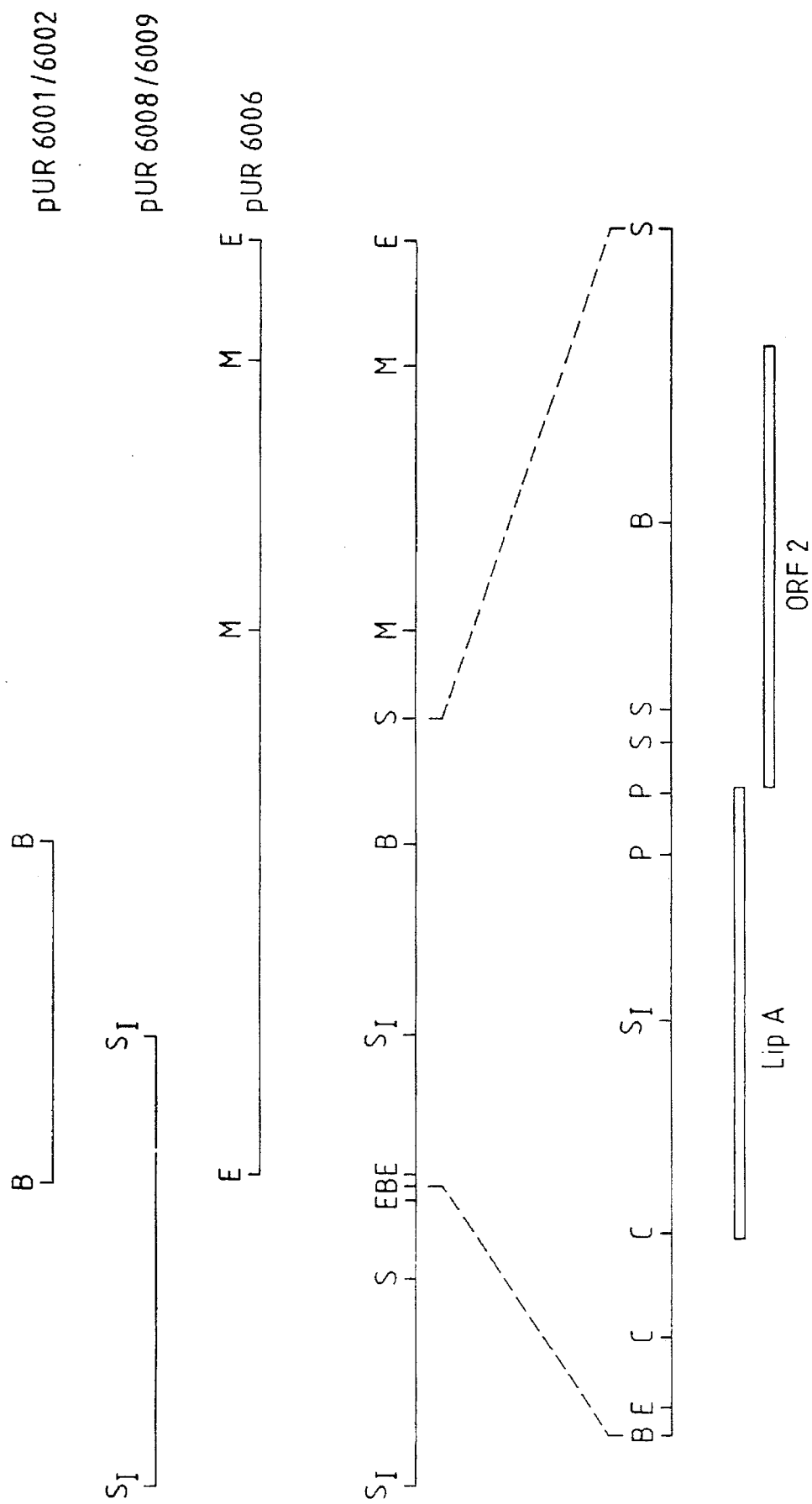

The microorganism capable of producing lipase can be a homologous or heterologous host for the expressible lipase gene. For example, when *Pseudomonas glumae* is used as a Gram negative host bacterium, its own homologous lipase gene can be used, preferably present in many copies. However, if another host is preferred, for example a *Bacillus subtilis*, because it is used by several manufacturers of detergent enzymes as a good producer of enzymes, the lipase gene from *P. glumae* is heterologous to the *Bacillus subtilis*. Besides the expressible lipase gene, the transformed microorganism of the present invention also contains a lipase-specific stabilization/translocation protein.

The microorganism which is to be transformed can be selected from the group consisting of:

(a) Gram negative bacteria, including members of the family of the Pseudomonadaceae, preferably of the genus Pseudomonas, more preferably of the species *P. cepacea, P. gladioli, P. glumae, P. mendocina, P. putida* and *P. stutzeri;*

(b) Gram positive bacteria, including members of the family of the Bacillaceae, preferably of the genus Bacillus; and (c) eukaryotes, including members of the yeast genera Hansenula, Kluyveromyces, Pichia, Saccharomyces, and the mould genera Aspergillus, and other lower eukaryotes.

A suitable Gram negative bacterium, from which either one or both above-mentioned genes can originate, is a member of the family of the Pseudomonadaceae, preferably of the genus Pseudomonas, more preferably of the species *P. cepacea, P. gladioli, P. glumae, P. mendocina, P. putida* and *P. stutzeri*.

The preferred lipase gene encodes either the lipase from *P. glumae* PG1 or a lipase showing immunological cross reactivity with an antiserum raised against a lipase from *Chromobacter viscosum* var lipolyticum NRRL B-3673, or against a lipase from Alcaligenes PL-679, ATCC 31371 or FERM-P 3783, or against a lipase from *Pseudomonas fluorescens* IAM 1057.

Because improvements in the perfomance of lipase in detergent compositions are still desirable, preference is given to a microorganism according to the invention, in which the gene encoding the lipase is a modification of a wild type lipase gene, e.g. as those described in copending EP-A-407 225. Such modification is obtainable with recombinant DNA techniques, including site-directed mutagenesis methods, in order to improve the lipase efficiency in detergent or cleaning systems without the corresponding modified lipase impairing the stabilization/translocation function of the lipase-specific stabilization/translocation protein. Thus the invention also relates to the production of modified lipases having an improved performance in detergent systems.

A preferred lipase-specific stabilization/translocation protein is that isolated from *Pseudomonas glumae* PG1, specifically when it is used with the lipase gene from *Pseudomonas glumae* PG1, but other lipase-specific stabilization/translocation proteins having essentially the same stabilizing/translocating activity can also be used. For example, a lipase-specific stabilization/translocation protein can be used whereby the protein or its gene is identical to or has substantial (sequence) homology with the lipase-specific stabilizing/translocating protein or its gene originating from *Pseudomonas glumae* PG1 as herein described.

Furthermore, lipase-specific stabilizing/translocating protein can be used which show an immunological cross reactivity with an antiserum raised against the lipase-specific stabilization/translocation protein, or its epitopes, from *Pseudomonas glumae* PG1, provided that they have a similar stabilization/translocation action. Genes coding for stabilization/translocation proteins of lipases produced by Gram negative bacteria can easily be isolated by means of known methods, such as PCR-technology.

One way of obtaining an improved lipase production is to prepare a microorganism containing a mutation in the sequences regulating the transcription, particularly in the promoter and controlling an operon comprising two genes which after transcription results in a polycistronic messenger RNA for both a lipase and a lipase-specific stabilization/translocation protein, such that the promoter activity is at least doubled compared with the activity in the wild type. Another possibility is to replace the original promoter sequence in front of these genes by a stronger and more suitable promoter, e.g. the strong and inducible tac promoter. Of course, combinations of these alternatives can be used. This improved regulation of the transcription or promoter activity can result in a larger production and secretion of the lipase.

As shown in the Examples below it was found that the stability of the expression plasmid containing the lipase gene construct and/or its mRNA could be improved when the lipase gene is preceded by a gene fragment encoding a signal sequence, preferably homologous to the host cell, containing between said signal sequence and said lipase gene a stretch of nucleotides encoding the C-terminal part of the signal sequence of the lipase, preferably not more than 45 nucleotides, more preferably not more than 24 nucleotides from the C-terminal part, especially one of the stretches of nucleotides given in FIGS. 2A–2J, whereby the stretch has so many nucleotides that the lipase gene is in the reading frame determined by the ATG (start) codon of the signal sequence homologous to the host cell. Although the invention is not limited by theoretical considerations, it is believed that the amino acids encoded by this stretch are important for a good translocation and correct processing of the pre(pro) lipase into lipase.

The invention further provides a process for producing a lipase-producing microorganism as described above, in which recombinant DNA modification methods are used for transforming a microorganism such, that both at least one copy of a gene encoding a lipase and at least one copy of a gene encoding a lipase-specific stabilization/translocation protein are introduced into said microorganism, whereby the latter gene can be expressed in said microorganism in concert with the expression of the lipase gene. The number of gene copies can be regulated by the choice of the vector or by multicopy integration on the chromosome of the host.

In a preferred process both genes are introduced as an operon comprising two genes which after translation results in a polycistronic messenger RNA for both a lipase and a lipase-specific stabilization/translocation protein. Although the most direct method for a process for obtaining an improved lipase production in a lipase-producing microorganism according to the invention is the use of recombinant DNA methods, it is also possible that a positive mutation is obtained by classical mutation.

The two genes may be linked to each other in a two-gene operon, but they can also be applied as two separate genes under control of strong promoters, which may be the same or different. If different promoters are used it is important to induce these promoters in concert. When applied as separate genes they can be present either on the same or different plasmids, or in the chromosome of the host. This applies to both homologous hosts and heterologous hosts, in particular for lower eukaryotes.

Another aspect of the present invention is a nucleotide sequence encoding a lipase-specific stabilization/translocation protein, preferably originating from a lipase-producing Gram negative bacterium. In particular, the invention provides a sequence encoding a lipase-specific stabilization/translocation protein as given in FIG. 3. It was further found that the ORF2 gene contains a stretch of about 200 nucleotides having a very high G+C content. This appeared to give problems in hosts which are considered heterologous to P. glumae as is explained further in the Examples below.

Therefore, for a heterologous host the part of the gene having the very high G+C content is preferably modified such that the G+C content and the codon usage is in agreement with the G+C content and codon usage of well expressed genes in that host. In the Examples it is illustrated that this can be achieved by modifying that part of the ORF2 gene encoding the first about 200 amino-acids of the lipase-specific stabilization/translocation protein.

Thus in order to improve the stability of the expression plasmid and/or the mRNA the first about 200 codons of that nucleotide sequence can be modified such that they encode essentially the same amino acids, but have a G+C content equal or nearly equal to that of messenger RNA's that are translated very well in the host cell considered. In a modification of this embodiment the total ORF2 sequence has a G+C content essentially equal to the G+C content of messenger RNA's that are translated very well in the host cell considered for expressing said sequence. Replacement of the G+C rich stretch can also be advantageous for homologous hosts.

A further embodiment of the invention is a process for producing a lipase by a transformed microorganism, in which a transformed microorganism according to the invention as described above is cultivated under conditions whereby the lipase is produced and preferably secreted, and subsequently the lipase is collected.

Finally, the invention relates to a detergent or cleaning composition containing a lipase produced by, and preferably isolated from, a microorganism according to the invention.

The present invention is illustrated by the following Examples. The techniques used are essentially as described in e.g. J. Sambrook, E. F. Fritsch, and T. Maniatis; Molecular Cloning: a Laboratory Manual; 2nd Ed. (1989) Cold Spring Harbor Laboratory Press or in copending but still unpublished patent specifications EP-A-407 225 and WO-A-91/00920.

EXAMPLE 1

Isolation of the ORF2 Gene of P. glumae PG1

A genomic library of P. glumae PG1 was constructed in cosmid vector c2RB (Bates and Swift, 1983) maintained in E. coli 1046 (met, gal, lac, hsdR, phx, supE, hsdM, recA). To isolate the lipA gene, the library was screened with radiolabeled mixed probes, based on the $NH_2$-terminal amino acid sequence of the P. glumae lipase. In this way several positive cosmid clones were obtained, one of which was named pUR6000. From this cosmid clone several subclones were prepared, amongst others pUR6001, pUR6002 and pUR6006, which also gave a positive reaction with the radiolabeled mixed probes. The preparation of these plasmids was described more extensively in copending but still unpublished patent specifications EP-A-407 225 and WO-A-91/00920, in which also the complete nucleotide sequence of the lipA structural gene was described. It was found that this gene encodes a lipase-precursor containing an N-terminal extension of 39 amino acids preceding the mature lipase. It was assumed that this extension functions as a secretion signal of the lipase, although it was considered to be relatively long for a signal sequence.

Further research on the DNA sequence downstream of the lipA gene present on an about 2.2 kb BamHI fragment, present in pUR6001 and pUR6002 described in copending EP-A-407 225, has now shown that immediately downstream of the lipA gene an ATG (start) codon is present (position 1559). This ATG is preceded by a putative RBS and followed by a open reading frame (ORF2), which apparently extends beyond the downstream BamHI site, because in the ORF2 part of the BamHI fragment no stop codon was found.

In order to determine the complete sequence of ORF2 it appeared to be possible to make use of the presence of some SacII sites in pUR6006, because restriction enzyme analysis showed that a SacII fragment of about 1.2 kb is present containing the BamHI site downstream of the lipase gene. Therefore, a plasmid pUR6026 was made by replacing the multiple cloning site of plasmid pEMBL9 (Dente, L. et al., 1983) by an EcoRI-HindIII fragment containing one SacII site and one BglII site between the EcoRI site and the SacII site. The about 1.2 kb SacII fragment of pUR6006 was subcloned in the unique SacII site of pUR6026, resulting in two plasmids each having the SacII fragment in a different orientation (pUR6012A and pUR6012B; see FIG. 1). Determination of the correct plasmid (pUR6012A) was carried out as described in Example 5 below using appropriate restriction enzymes.

From sequence analysis of this SacII fragment combined with the sequence data obtained earlier from the BamHI fragment of pUR6001 and pUR6002 it was concluded that the ORF2 is 1062 bp long (see FIG. 2) and encodes a protein of 353 amino acids (see FIG. 3). FIG. 4 represents the chromosomal situation around the lipA gene as deduced from several restriction maps (not all are given) and the above indicated sequence data.

The start codon of ORF2 overlaps with the stop codon of the lipA gene (TGATG). This phenomenon of overlapping or closely adjacent TGA and ATG codons was found in earlier cases (Brunel 1988, Givskov 1988, Zylstra 1989, and Noda 1990) and are indicative for neighbouring cistrons transcribed on a polycistronic mRNA. In front of the start codon of ORF2 no promoter sequence could be detected, although a putative sequence that could serve as ribosome binding site (RBS) was found as mentioned above.

The codon usage of ORF2 (position 1559–2617) as can be derived from FIG. 2 corresponds with the codon preference table for *P. aeruginosa* (West and Iglewski, 1988). The G+C contents of the total ORF2 is 77% (G+C on third position= 91.5%), which is in the common range for Pseudomonaceae. Remarkably, however, is the stretch of about 200 bp (from about 1680 to about 1880) having an extremely high G+C content of 89%. This stretch might form strong stem-loop structures due to the presence of inverted repeats. Stem-loop structures of this kind might regulate mRNA degradation and be responsible for differential gene expression as was published before (Chen 1988, Brawerman 1990).

Thus this Example results in the DNA sequence of ORF2 and the amino acid sequence encoded by it as given in FIGS. 2 and 3, respectively.

EXAMPLE 2

Junction of the ORF2 Gene Product

To study the function of ORF2 a specific inactivation of this gene has been carried out. Disruption of ORF2 is achieved by insertion of the tetracycline resistance gene of pBR322 (located on an about 1.4 kb EcoRI-AvaI fragment), into the unique BamHI site of pUR6012A (see Ex. 1) after filling in the sticky ends of the vector and the fragment (see FIG. 1). The resulting plasmid was called pUR6200 and contains a BglII site present in pUR6012 and originating from the inserted EcoRI-HindIII fragment of pUR6026 (see Ex. 1). Plasmid pUR6200 was digested with BglII and partially with HindIII and the digestion mixture was cloned into the unique BamHI site of pRZ102 (Jorgensen et al, 1979) after filling in the sticky ends. The ligation mixture was transformed to *E. coli* S17-1 and plated on LB agar containing kanamycin (25 mg/l) and tetracycline (25 mg/l). From the colonies obtained a plasmid coded pUR6208 was isolated carrying an insert of about 2.6 kb comprising the chromosomal SacII fragment with the inserted Tc-resistance gene.

Introduction of pUR6208 into *P. glumae* PG1 was achieved via biparental mating with *E. coli* S17-1 (pUR6208) and selecting for transconjugants on MME plates (0.2 g/l $MgSO_4$-$7H_2O$, 2 g/l Citrate-$H_2O$, 10 g/l $K_2HPO_4$, 3.5 g/l $NaNH_4HPO_4$·$4H_2O$, 0.5% glucose and 1.5% agar) supplemented with 80 mg/l tetracycline. According to the results obtained after transferring several transconjugants to MME-Km (100 mg/l), MME-Tc (80 mg/l) and to BYPO-Tc plates (10 g/l trypticase peptone, 3 g/l yeast extract, 5 g/l beef extract, 5 g/l NaCl, 7 g/l $KH_2PO_4$, 50 ml/l olive oil emulsion and 1.5% agar with 80 mg/l tetracycline), three different phenotypes could be identified namely:

(a) Tc-res, Km-sen, Lip⁻, (b) Tc-res, Km-res, Lip⁻ and (c) Tc-res, Km-res, Lip⁺.

Southern analysis of these strains revealed that in case of (a) a double crossover had occurred resulting in the replacement of the intact ORF2 gene by a disrupted gene, (b) a single crossover had occurred at the 5' region of the SacII fragment, and (c) a single crossover had occurred at the 3' region of the SacII fragment, respectively.

A representative of type (a) transconjugants was termed *P. glumae* PG4, and was used for further investigations. After growing PG4 on BYPO plates for ten days no clearing zone was detectable, proving that even after prolonged incubation no active lipase was produced by PG4, whereas PG1 under the same conditions already after about five days showed a clearing zone indicating the formation and secretion of lipase.

The PG4 mutant was also used to study the effects of the inactivation of ORF2 on the physiology of *P. glumae* and on the translocation of proteins, especially on that of LipA. Comparisons of the growth of PG1 with that of PG4 in PG-medium (($NH_4)_2SO_4$ 6 g/l, $KH_2PO_4$ 3.5 g/l, $K_2HPO_4$ 3.5 g/l, $CaCl_2$ 0.02 g/l, yeast extract 2 g/l, $MgSO_4$·$7H_2O$ 1 g/l and trace elements (Egli, 100×) 10 ml/l. pH 6.5) supplemented with either 0.5% glucose or 0.5% oleic acid did not reveal any difference. This is in agreement with the fact that growth of the bacteria in the presence of glucose or oleic acid as carbon source can occur without the necessity of lipase being formed.

Figure 5:
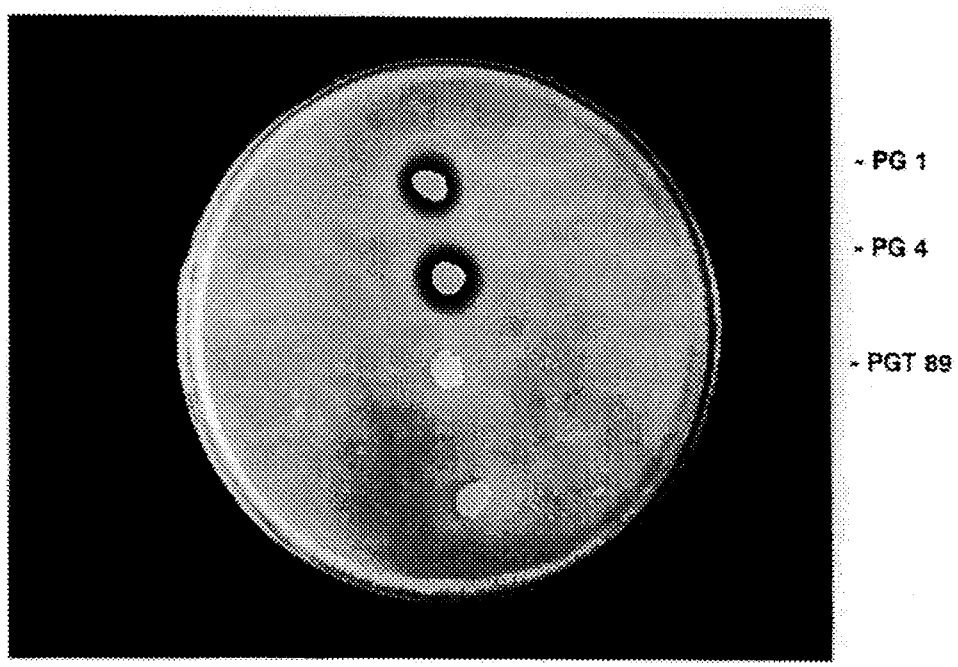

Secretion of protease on skim milk plates were also similar (FIG. 5). This means that the ORF2 gene product does neither influence the (lipid) metabolism nor the common protein secretion system of *P. glumae* and indicates that ORF2 is very specific for stabilization/translocation of just lipase. After cultivation of either PG1 or PG4 in PG/oleic acid medium and analyzing the mRNAs of these cultures by means of Northern analysis, it was found that in both cases a mRNA band of about 1400 nucleotides was present (FIG. 6) that hybridizes with the PvuII fragment of the lipA gene, corresponding with the nucleotides 792–1472 (FIG. 2). This indicates that neither the ORF2 gene nor any possible ORF2 gene product is involved in the transcriptional regulation of the lipA gene. After growth of PG4 cells under lipase-inducing conditions, i.e. in PG/oleic acid medium, neither in the cells nor in the culture medium lipase could be detected by means of Western analysis, whereas for PG1 lipase could be detected in both the cells and the culture medium.

As the amount of mRNA encoding lipase in PG1 and PG4 is about the same and no changes in the nucleotide sequences of the lipase gene that may influence the efficiency of translation were introduced, it can be concluded that the ORF2 gene product is essential for the stabilization/translocation of lipase in *P. glumae*.

EXAMPLE 3

Complementation of the Lipase Production of *P. glumae* PG4

Plasmids pUR6500, pUR6502 and pUR6522 were described on pages 80–82 of copending EP-A-407 225 mentioned above. Plasmid pEM4 was obtained by replacing the EcoRI-HindIII multiple cloning site of pEMBL9 (see above in Example 1) by a synthetic DNA fragment having the following sequence

AATTCTGCAGTGGCAGACACGCGTA(SEQ ID NO:1)
GACGTCACCGTCTGTGCGCATTCGA(SEQ ID NO:2)

This new multiple cloning site contains the following restriction sites in the order given: EcoRI (GAATTC), PstI (CTGCAG), MluI (ACGCGT), HindIII (AAGCTT). Plasmid pUR6098 was made by cloning the about 2 kb PstI-MluI fragment present in pUR6006 (see above in Example 1 and FIG. 4) into pEM4 digested with the same two restriction enzymes. From pUR6098 the about 2 kb EcoRI-HindIII fragment was cloned in pUR6500, digested with the same two restriction enzymes, resulting in pUR6520. As host for the cloning procedure E. coli JM109 was used.

The plasmids pUR6500, pUR6502, pUR6520 and pUR6522 were separately introduced into P. glumae PG4 by biparental matings. For control purposes plasmids pUR6500 and pUR6522 were also introduced separately in the wild type P. glumae PG1 in the same way.

Following selection of the transconjugants on MME-Km plates containing 100 mg/l kanamycin, they were transferred to BYPO-Km plates containing 100 mg/l kanamycin with and without 0.5 mM isopropyl-thiogalactoside (IPTG). After incubation for one week at 30° C. the lipase production was evaluated (Table 1 and FIG. 7). Curing experiments of PG4 containing pUR6500, pUR6520 or pUR6522 showed that no integration by homologous recombination had taken place.

Figure 8:
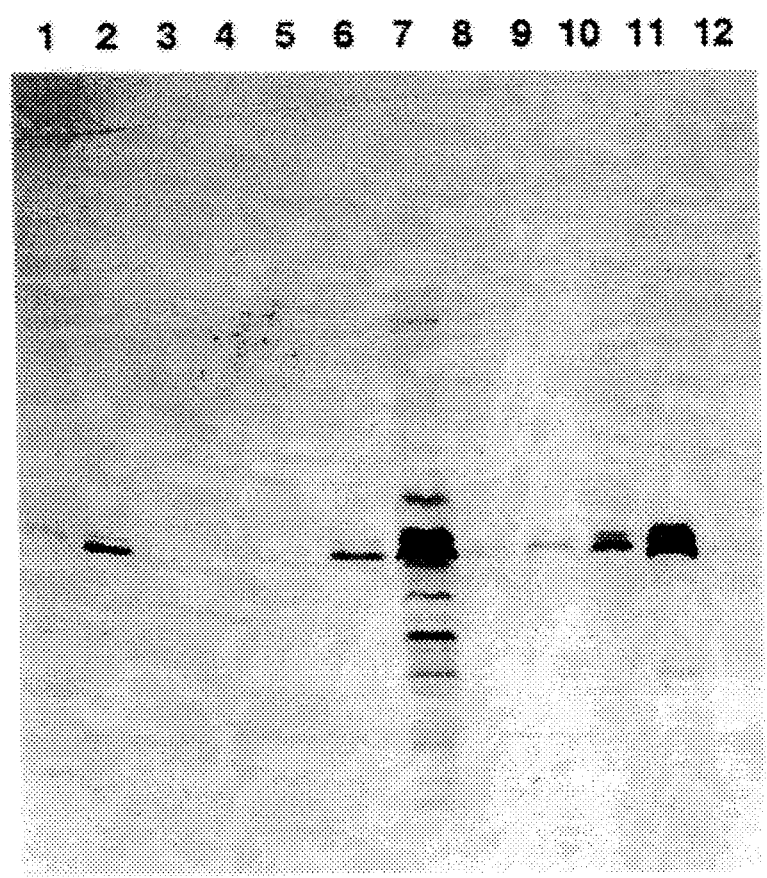

The results of Western analysis of PG4 cells containing the above given 4 plasmids grown in PG/oleic acid medium are given in FIG. 8, in which also the results of PG1 containing pUR6500 are presented as a control of the wild type lipase-producing bacterium transformed by a plasmid not containing chromosomal DNA from P. glumae.

The results of these experiments show that it appeared possible to express the ORF2 gene in PG4 in two ways, both resulting in the production of a protein mediating the stabilization/translocation of lipase in P. glumae.

One way was by translation from a polycistronic mRNA encoding both Lipa and the ORF2 gene product (originating from pUR6522). The other was translation from an mRNA encoding only ORF2 (originating from pUR6520), while the lipase was translated from another mRNA encoding the LipA (originating from the chromosome, in which the ORF2 wag inactivated by the insertion of the Tc-resistance gene). Strain Pseudomonas glumae PG4 (pUR6520) was deposited at the Centraalbureau voor Schimmelcultures, Baarn, The Netherlands under number CBS 405.90 on 18 Sep. 1990.

EXAMPLE 4

Improved Expression and Secretion of Lipase

The production of lipase under its own promoter in a liquid culture has several disadvantages such as the relatively low productivity and the production of other components like proteases and glycolipids, which has a negative effect on the down-stream processing for isolating the lipase in a form suitable for application in detergent systems.

One way to decrease these problems is to use another (preferably inducible and preferably stronger) promoter to improve the expression of the lipase operon (containing both lipA and ORF2). Therefore, an experiment was carried out with plasmid pUR6522 in which the complete lipase and the ORF2 gene are placed under the inducible tac promoter. As a control plasmid pUR6500 was used, which does not contain chromosomal DNA from P. glumae but contains the same expressible Km-resistance gene as is present in pUR6522.

Figure 9:
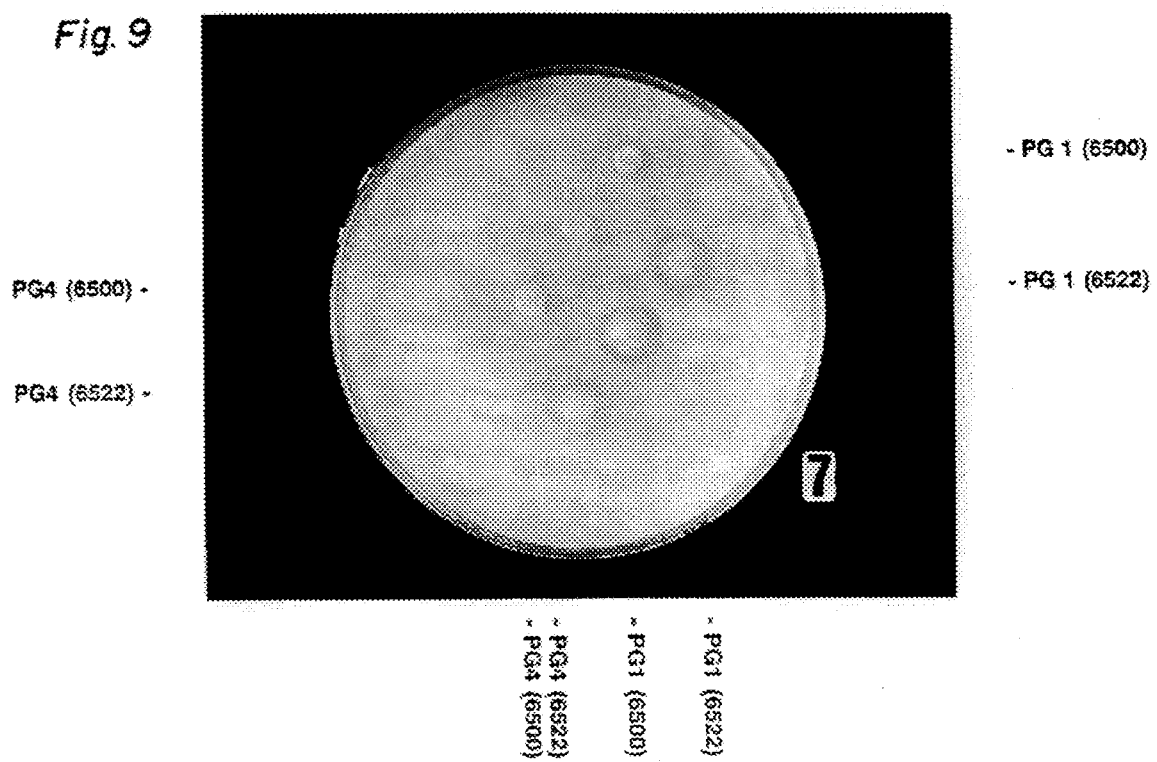

As shown in FIG. 9 the amount of lipase produced by either P. glumae PG4 (pUR6522) or wild type P. glumae PG1 (pUR6522) is indeed higher then in a similar experiment with P. glumae PG1 (pUR6500) or P. glumae PG4 (pUR6500). Moreover, the purification of the lipase produced by the pUR6522-containing strains may be easier.

EXAMPLE 5

Lipase Expression in E. coli

A plasmid called pUR6518 was obtained by cloning the about 1,8 kb EcoRI fragment of pUR6502 into pMMB67EH (Fürste, 1986) also digested with EcoRI. Since the fragment could be inserted in two different orientations, the correct orientation (with respect to the tac promoter) had to be selected. For this purpose the plasmids containing the EcoRI fragment were digested with BamHI and the fragments obtained were identified by agarose gel electrophoresis. This enabled to determine a construct bearing the EcoRI fragment in the desired orientation, which was designated pUR6518. E. coli JM109 was transformed with plasmids pUR6518, pUR6522, pUR6518+pUR6520, or as a control pUR6500, and the transformants were grown on BYPO-plates (with or without IPTG).

None of the transformants had a clearing zone that was visible, showing that no biologically active lipase was secreted. To exclude construction errors or deletions in the plasmids, plasmids were isolated and subjected to restriction enzyme analysis. All plasmids appeared to be intact and could be maintained stable in E. coli JM109. Further experiments with the obtained strains are described below.

E. coli JM109 (pUR6518)

Figure 10:
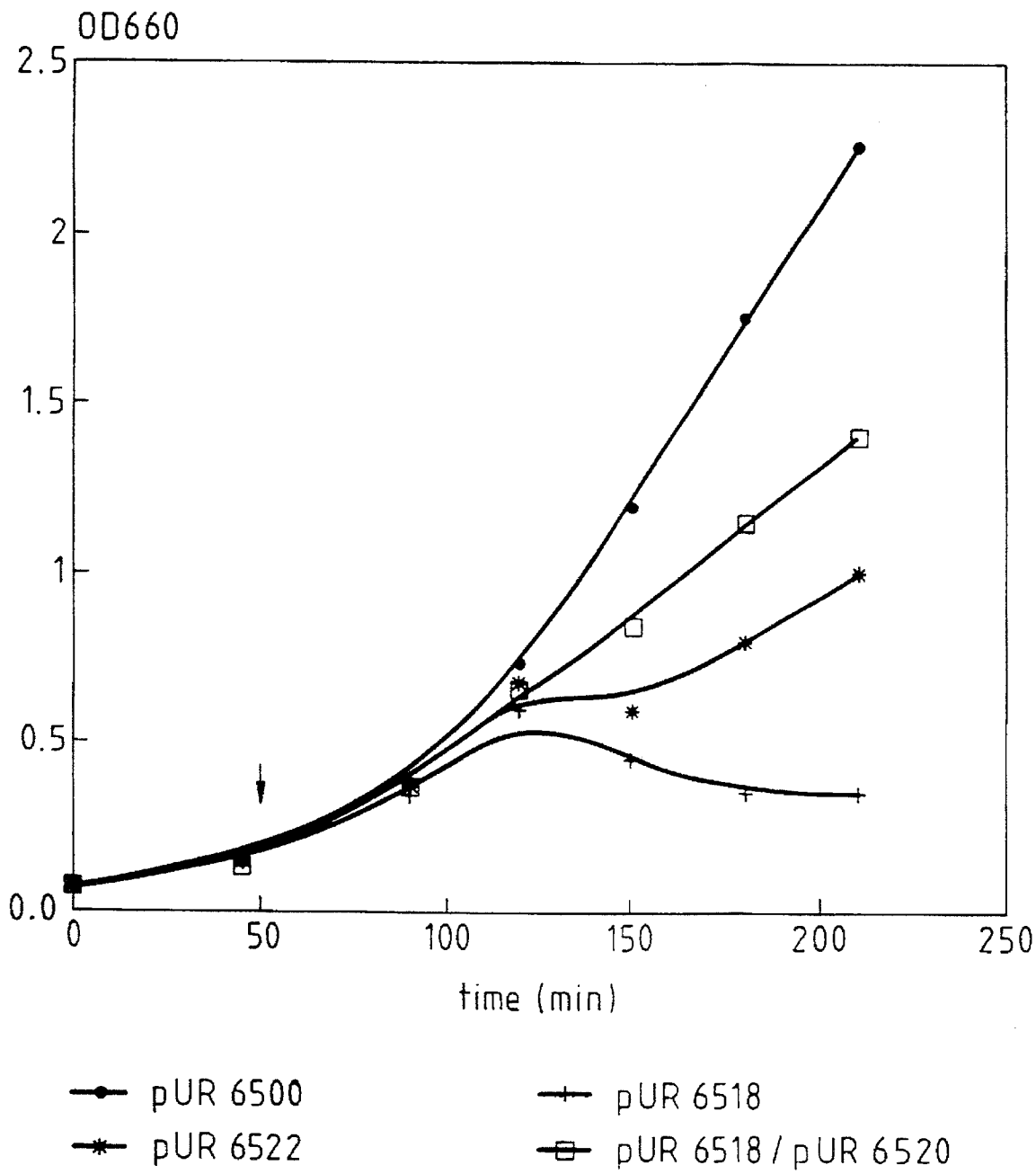

Growth experiments of E. coli JM109 (pUR6518) in LB-medium were performed by diluting an overnight culture to an OD660 of about 0.15. After 1.5 hours of growth, IPTG was added to a final concentration of 0.2 mM to induce the tac promoter followed by an incubation for another 2 hours. Compared to non-induced control cultures (strains with either pUR6518 or pUR6500; results not shown), the addition of IPTG had a dramatic influence on the cell growth (FIG. 10).

No lipase activity could be detected in the culture medium, when assayed by means of the pH-stat technique. This technique comprises following the formation of free fatty acids in a pH-stat (PHM84 Research pH meter, ABU80 auto-burette and TTA60 titration assembly ex Radiometer, Copenhagen, and an Apple II computer for data handling) at pH=9.0 and 30° C. Titrant was 0.05N NaOH (Titrisol ex Merck).

Northern analysis from isolated mRNA using as a probe the PvuII fragment derived from lipA gene (see Example 2) showed mainly two bands, one of about 1400 and the other of about 2300 nucleotides. Northerns using as a probe the NruI fragment of ORF2 (nucleotides 1854 to 2524, see FIGS. 2A–2J) showed also a band corresponding to about 2300 nucleotides (FIGS. 11A–11B).

From Western analysis of induced cells (see FIG. 12) it appeared that intracellular lipase was present. FIG. 10 shows a dramatic decrease of the OD660 indicating strong cell lysis. Although some lipase was found in the culture medium, this is due to the cell lysis, whereby at least part of the cell content is released in the culture medium.

Furthermore, after pelleting the cells of *E. coli* JM109 (pUR6518) present in 50 ml culture broth by centrifugation and resuspending the cell pellet in 1 ml of a salt solution (0.9% w/v), followed by treating with a French press to disrupt the cells and storing the resulting material overnight at 4° C., it was surprisingly found that small amounts of lipase activity could be measured by the pH-stat technique, although immediately after disrupting the cells no lipase activity was found. This proves that translation of the lipase mRNA to the corresponding protein occurs, but an inactive form is produced. Under certain conditions this inactive form appears to be capable of refolding to the active form.

*E. coli* JM109 (pUR6522)

To determine whether the ORF2 gene is expressed in *E. coli* as a functional protein, plasmid pUR6522 was introduced in *E. coli* JM109. Transformed cells were subjected to the same set of experiments as described above giving the following results.

Northern analysis using the PvuII probe derived from lipA resulted in detecting two bands with a length of about 1400 and 2600 nucleotides. The last one is long enough to encode both lipA and the complete ORF2. This was confirmed by using the NruI probe derived from ORF2 (FIGS. 11A–11B), which showed a broad band between about 2600 and 1800 nucleotides.

The Western analysis of the cell extract showed that a considerable amount of lipase was produced. Western analysis of the culture medium did not reveal any lipase (see FIG. 12). In this respect *E. coli* differs clearly from *P. glumae*. This unexpected result can be explained by a high instability of the poly-cistronic mRNA and/or by an insufficient translation of the ORF2 gene messenger in *E. coli*.

Although the presence of the ORF2 gene in *E. coli* does not result in a detectable amount of lipase in the culture medium, at least not detectable by Western analysis or pH-stat technique, a significant difference in growth and lysis of *E. coli* cells carrying a plasmid with the lipA gene and either with ORF2 (pUR6522) or without ORF2 (pUR6518) was observed. Cells without the ORF2 gene grow poor and lyse fast, indicating that lipase was produced and blocked or destroyed the cell membrane in the absence of ORF2 gene product. Cells with the ORF2 gene product only show a stagnation in growth but no lysis as is clear from the lack of lipase product in the culture medium shown in FIG. 12.

*E. coli* JM109 (pUR6518+pUR6520)

*E. coli* JM109 was transformed with pUR6520 and pUR6518 together and subjected to the same experiments as above in order to test the above suggested possibilities of a high instability of the polycistronic mRNA and/or of an insufficient translation of the ORF2 gene messenger in *E. coli*. The strain containing both plasmids does not show any stagnation in growth, although the growth rate is still somewhat less than that of the control strain containing pUR6500. No indications for cell lysis were found. However, active lipase could not be detected, neither on BYPO plates, nor in the culture medium. Northern analysis using the NruI probe showed one clear band with a length of about 1200 nucleotides (FIGS. 11A–11B).

Figure 12:
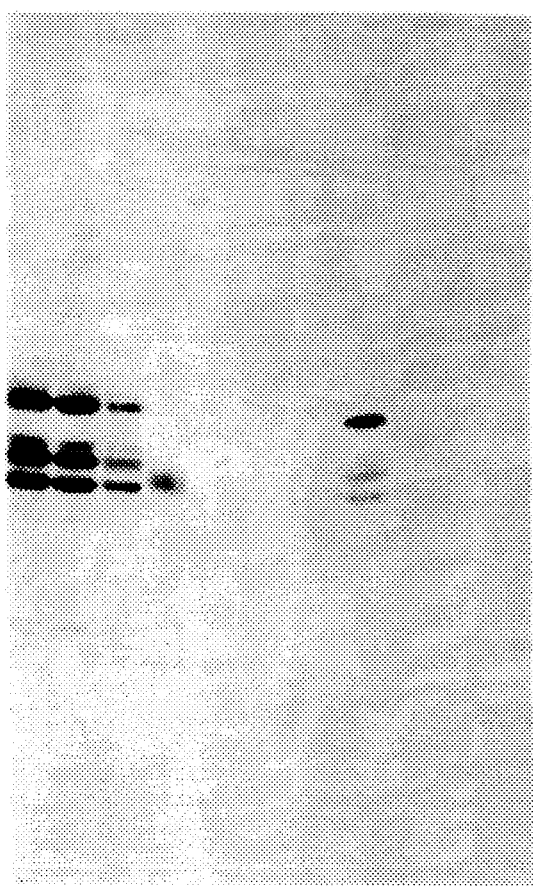

Western analysis of lipase in the medium was negative, but lipase could be detected in the cell (FIG. 12). From these experiments with pUR6518, pUR6522 and pUR6518+pUR6520 it can be concluded that (1) the stability of the polycistronic LipA/ORF2 messenger is poor in *E. coli* in view of the results of the Northern analysis, (2) either the transcription of ORF2, or the stability of the ORF2 mRNA, or both, may not be very good, (3) for both messengers the translation of the ORF2 seems to be not very efficient due to the stretch of about 200 nucleotides with a high G+C content present in the ORF2 part of the mRNA; such high G+C content is unusual for *E. coli*.

Strains *E. coli* JM109 (pUR6518), *E. coli* JM109 (pUR6520) and *E. coli* JM109 (pUR6522) were deposited at the Centraalbureau voor Schimmelcultures, Baarn, The Netherlands under numbers CBS 406.90, CBS 407.90 and 408.90, respectively on 18 Sep. 1990.

EXAMPLE 6

Lipase Expression in *P. putida* WCS358

The strain *P. putida* WCS358 has been chosen as this strain does not produce a lipase, neither it has a gene that hybridizes with a DNA probe derived from lipA gene. Plasmids pUR6500, pUR6502 and pUR6522 were introduced into *P. putida* by biparental matings, whereby pUR6500 was used as a control (cf. Examples 3–5).

*P. putida* WCS358 (pUR6502)

After growing transconjugants containing pUR6502 in BHI medium containing IPTG and measuring the activity with the pH-stat technique described in Example 5 above, no lipase activity could be detected. However, on BYPO plates containing IPTG a small clearing zone became visible after prolonged incubation. This is probably due to release of lipase after starvation and subsequent lysis of cells.

Western analysis of the cell material of these transconjugants yielded the same results as for *E. coli* (pUR6518), i.e. lipase was produced but not secreted. This means that *P. putida* WCS358 lacks the ability to express a gene functionally related to the ORF2 gene product. Even under conditions where in addition to IPTG also fatty acids are present (that normally are capable of inducing the production of proteins related to the lipase synthesis and fatty acid metabolism), *P. putida* is still not capable of secreting lipase formed by the expression of the lipase gene present in pUR6502. Apparently, this is due to the absence of the ORF2 gene product from *P. glumae* PG1, or a functionally equivalent product from *P. putida* WCS358. This means that the function of the ORF2 gene product is quite unique, even in Pseudomonads.

*P. putida* WCS358 (pUR6522)

Several of the transconjugants obtained after introduction of pUR6522 were transferred to BYPO-Km-IPTG plates. After incubation for about five days at 30° C. clearing zones became visible in four out of ten colonies. These four lipase positive colonies were cultivated on brain-heart-infusion (BHI) medium (ex DIFCO) and induction was performed by addition of IPTG (to a final concentration of 0.2 mM). One of these four induced strains was further investigated and appeared to have secreted lipase in an active form as shown with the pH-stat technique.

Western analysis of this strain confirmed the presence of lipase in both the cell extract and the medium. Thus, *P. putida* WCS358 is able to translate the ORF2 gene from the polycistronic messenger and to secrete an active lipase, in contrast to *E. coli*. However, as only 4 out of 10 strains were capable of producing extracellular, active lipase, scope for further improvement is still available (see Example 8).

EXAMPLE 7

Lipase Expression in *Bacillus subtilis*

As Gram negative bacteria are not the most suitable bacteria for large scale production of enzymes we decided to test whether ORF2 has a positive influence on the production of the lipA gene product in a Gram positive bacterium, i.e. *Bacillus subtilis*. A plasmid pUR6785 was constructed that contains the ORF2 gene in addition to a complete lipase gene. This was accomplished as follows:

(1) Plasmid pUR6016 was obtained by ligating the about 2.1 kb EcoRI-BamHI fragment of pUR6002 (containing lipA and part of ORF2, described in copending EP-A-407 225) into the isolated EcoRI-BamHI fragment of pUR6012A described above containing the origin of replication.

(2) Plasmid pUR6781 was obtained by ligating the about 0.5 kb EcoRI-SalI fragment of pUR6038 (containing the 5' part of a synthetic lipase gene, described in copending EP-A-407 225) into the isolated EcoRI-SalI ori-containing fragment of pUR6016.

(3) Plasmid pUR6783 was obtained by ligating the about 2.5 kb EcoRI-HindIII fragment of pUR6781 (containing a partly synthetic/partly wild type lipA gene and the complete wild-type ORF2 gene) into the isolated EcoRI-HindIII ori-containing fragment of pMS51. The latter plasmid was obtained by replacing the EcoRI-HindIII multiple cloning site of pUC9 (J. Norrander et al., 1983) by a synthetic DNA fragment having the following sequence AATTTGGTAACCGGATCAGAAAGGAGGTGATCGAATTCAA(SEQ ID NO:3)
    ACCATTGGCCTAGTCTTTCCTCCACTAGCTTAAGTTTCGA(SEQ ID NO:4)

comprising a sticky end compatible with that of the EcoRI site, a BstEII site (GGTNACC), RBS (GGAGG), EcoRI (GAATTC), and a the remainder of a HindIII site.

(4) From pUR6783 the about 2.5 kb BstEII-HindIII fragment (containing said lipA gene and said ORF2 gene preceded by a synthetic RBS) was ligated into the BstEII-HindIII ori-containing fragment of plasmid vector pMS48 (see EP-A-157 441) resulting in plasmid pUR6785.

Transformed *Bacillus subtilis* DB105 (spo⁻) strains containing either the stable plasmid pUR6773 (mentioned in the copending EP-A-407 225) or pUR6785 were grown on BYPO plates. *Bacillus subtilis* DB105 (pUR6773) strain was deposited at the Centraalbureau voor Schimmelcultures, Baarn, The Netherlands under number CBS 444.90 on 17 Oct. 1990. After about five days it was found that pUR6773-containing colonies did not gave a clearing zone, whereas the pUR6785-containing colonies showed a significant clearing zone (see FIG. 13).

Western analysis of cell material obtained after growing the strains overnight in LB medium supplemented with 25 mg/l kanamycin showed, that *Bacillus subtilis* cells containing either pUR6773 or pUR6785 contain lipase. On investigation of the supernatant of *Bacillus subtilis* (pUR6785) the presence of lipase was detected by Western analysis. *Bacillus subtilis* (pUR6773) proved to be unacceptable as a production strain, because it lysed very fast when growing in the liquid LB medium.

After cultivating the *Bacillus subtilis* (pUR6785) strain in a lab scale fermentor under conditions identical to those used for the production and excretion of guar α-galactosidase by *Bacillus subtilis* (Overbeeke et al., 1990), a sample was taken after about 48 hours. This sample was diluted up to $10^{-10}$ and the dilutions were transferred to BYPO plates containing 25 mg/l kanamycin. Surprisingly it was found that after about a week incubation at 37° C. only less than 10% of the colonies showed a clearing zone. After this observation plasmids were isolated from both a good-producing strain and a non-producing strain, and subjected to restriction enzyme analysis. This resulted in the finding that the plasmid in the non-producing strains had lost a DNA fragment of about 0.4 kb originally located in the PstI-BamHI fragment of ORF2 (see FIG. 14). This fragment overlaps with the earlier mentioned about 200 bp having a very high G+C content. Therefore, it is recommended to replace this G+C rich DNA fragment by a synthetic fragment which is more stable at least in Bacilli, as described in Example 8.

EXAMPLE 8

Replacement of the GC Rich Stretch at the 5' End of the ORF2 Gene

Results obtained in the Examples 5–6 disclosing difficulties in the expression of lipase gene combined with ORF2 in *E. coli* and *P. putida* strongly suggested that the G+C rich part of the ORF2 is the cause of these problems. For *Bacillus subtilis* this has been proven in the previous example. A solution to overcome these problems may be the replacement of at least part of the G+C rich DNA fragment of ORF2 by a fragment encoding essentially the same amino acids but having a lower G+C content. It is intended to use codons which (1) are more in line with the preferred codon usage of the host of interest and/or (2) reduce the possible formation of stem-loop structures. A preferred modification may be the complete adaptation of the ORF2 to the preferred codon usage of the host of interest. The methods used to synthesize such fragments of the ORF2 gene are essentially the same as described in copending EP-A-407 225 for the synthetic lipA gene. An example of such a synthetic sequence is given in FIG. 15.

Similar to the construction of a (partially) synthetic ORF2 gene for *Bacillus subtilis* and *E. coli*, such constructions can also be made for other host cells like *Saccharomyces cerevisiae*, *Hansenula polymorpha* and *Aspergillus niger*. Of course the preferences for certain codons may vary for the various hosts cells and consequently a number of synthetic fragments has to be made.

EXAMPLE 9

Construction of a Partially Synthetic lipB Gene Having a Lowered GC-content

The DNA sequences as presented in FIGS. 15A–15B and 16A–16B were assembled starting from synthetic oligonucleotides, using the cassette system as described in example 3 of copending patent application EP-A-407 225. The sequence as given in FIGS. 15A–15B was cloned into plasmid pUR6600 resulting in plasmid pET25. pUR6600 is a derivative of pEMBL9 containing the synthetic lipase gene and is described in example 3 of above mentioned patent application. Plasmid pUR6012A was digested with PvuI and HindIII in religated in the presence of synthetic oligonucleotides having the sequence:

CGTGGAGCAGGAGGTTAGTGACTGCAGTTACTA(SEQ ID NO:5)
TAGCACCTCGTCCTCCAATCACTGACGTCAATGATTCGA(SEQ ID NO:6)

resulting in plasmid pET33.

A. Construction of expression plasmids pUR6523 and pUR6524.

The ~430 bp PvuI/BamHI fragment of pET25 together with the EcoRI/PvuI linkers

AATTCATGGCGCAGGCCGAT(SEQ ID NO:7)
GTACCGCGTCCGGC(SEQ ID NO:8)

were ligated into the pET33 vector which was digested with EcoRI and BamHI and resulted in pET35. From this plasmid, which contains the partially synthetic lipB gene, the EcoRI-HindIII fragment (~1080 bp) was cloned into plasmid pMMB67EH (ampicillin resistance) and into pUR6500 (kanamycin resistance) resulting in pUR6523 and 6524, respectively. In these plasmids the expression of the partially synthetic lipB gene is under the control of the inducible tac promoter.

B. Construction of expression plasmid pUR6525.

The ~440 bp BamHI/HindIII fragment of pET33 was ligated into the pET25 vector, which was digested with the same enzymes. The resulting plasmid is named pET37 and contains the synthetic lipase gene followed by the partially synthetic lipB gene, located on a ~2160 bp EcoRI/HindIII fragment. This EcoRI/HindIII fragment was ligated into the expression vector pUR6500 and resulted in plasmid pUR6525, in which both genes are preceded by the inducible tac promoter.

EXAMPLE 10

Complementation of *P. glumae* PG4

Introduction of pUR6524 or pUR6525 into the PG4 strain resulted in a lipase producing phenotype when the cells were grown on BYPO plates supplemented with 0.5 mM IPTG. This finding is in agreement with Example 3 and proves that the partially synthetic lipB gene is functional.

Upon comparing the lipase production levels of *P. glumae* PG4 (pUR6522) and PG4 (pUR6525) is was furthermore found that the latter produces more lipase. This indicates that the replacement of the wild type lipase gene and part of the lipB gene by synthetic fragments, having a decreased G+C content, has a positive influence on the lipase production levels. In this way the improved production as described in example 4 is even exceeded.

EXAMPLE 11

Lipase Expression in *E. coli*

Upon introduction of pUR6525 into *E. coli* JM109 and growing the strain on BYPO medium supplemented with 0.2 mM IPTG and 25 µg/ml kanamycin, a clearing zone became visible after overnight incubation at 37° C. The same holds for *E. coli* JM109 containing (pUR6503+pUR6523) grown on BYPO medium supplemented with 0.2 mM IPTG, 100 µg/ml ampicillin and 25 µg/ml kanamycin.

It will be understood that other synthetically prepared genes encoding for these proteins or functional mutants thereof can also be used for obtaining improved lipase production.

EXAMPLE 12

Determination of the Role of the Amino Acids at the C-terminus of the Leader Sequence of Prelipase In our copending EP-A-407 225 mentioned above it was described that expression plasmids in which the gene fragment encoding mature lipase was preceded by either a gene fragment encoding the subtilisin prepro-sequence or the α-amylase pre-sequence, could not be stably maintained in *Bacillus subtilis* nor in other Bacillus strains. However, when using a mature lipase gene preceded by at least the last seven codons (thus at the C-terminus) of the 39 codons long pre-sequence, which in turn was preceded by the subtilisin BPN' pre-sequence, it was possible to prepare expression plasmids which were stably maintained in *Bacillus subtilis*. Moreover, lipase activity outside the cells could be detected.

In accordance with the present invention this example relates to the improved production of lipase in *Bacillus subtilis* by introducing into this host a plasmid containing both the ORF2 gene and a DNA fragment containing a homologous signal sequence followed by at least the part of the lipase gene encoding the mature lipase. One way of transforming this host can be introduction of plasmids pUR6766, pUR6767, pUR6768, or pUR6773 mentioned on page 64 of the copending EP-A-407 225, together with a second expression plasmid for ORF2 which can be stably maintained in that host. This approach would be analogous to the experiment(s) described in Example(s) 3 and 5 above. Alternatively, a Bacillus host can be transformed by introducing an expression plasmid for that host capable of expressing lipA and ORF2 from a two gene-operon through a polycistronic mRNA encoding both LipA and ORF2 gene product. For example, the synthetic lipase gene present in plasmids pUR6766, pUR6767, and pUR6768 can be replaced by a DNA fragment comprising in the order given (1) a leader sequence of a homologous *Bacillus subtilis* gene, (2) optionally, part of the C-terminus of the lipase leader sequence, (3) the DNA fragment encoding the lipase, (4) a stop codon, (5) ORF2, (6) a stop codon, and preferably (7) a transcription terminator. Of course, instead of the wild type gene fragment encoding mature lipase also modifications thereof can be used for investigating possible improvements of the lipase or its expression. The same holds for modifications of ORF2 and the leader sequences, or parts thereof.

REFERENCES MENTIONED IN THE SPECIFICATION

Bates, P. F. and Swift, R. A. (1983) Gene, 26 (1983) 137–146)

Bieker, K. L. and Silhavy, T. J. (1990) PrlA (SecY) and PrlG (SecE) interact directly and function sequentially during protein translocation in *E. coli*. Cell, 61, 833–842.

Brawerman, G. (1989) Mechanisms of mRNA decay. TIBTECH, 8, 171–173.

Brunel, F. and Davison, J. (1988) Cloning and sequencing of Pseudomonas genes encoding vanillate demethylase. J. Bacteriol., 170, 4924–4930.

Chen, C-Y. A., Beatty, J. T., Cohen, S. N. and Belasco, J. G. (1988) An intercistronic stem-loop structure functions as an mRNA decay terminator necessary but insufficient for puf mRNA stability. Cell, 52, 609–619.

Crooks, E, Guthrie, B, Lecker, S, Lill, R. and Wickner, W. (1988) ProOmpA is stabilized for membrane translocation by either purified E. coli trigger factor or canine signal recognition particle. Cell, 54, 1003–1011.

Dents, L. et al. (1983) Nucleic Acids Research, 11, 1645–1655 d'Enfert, C., Ryter, A. and Pugsley, A. P. (1987) Cloning and expression in Escherichia coli of the Klebsiella pneumoniae genes for production, surface localization and secretion of the lipoprotein pullulanase. EMBO J., 6 no. 11, 3531–3538.

d'Enfert, C. and Pugsley, A. P. (1989) Klebsiella pneumoniae pulS gene encodes an outer membrane lipoprotein required for pullulanase secretion. J. Bacteriol., 171, no. 7, 3673–3679, 1989.

Fürste, P. et al., (1986) Gene 48, 119–131.

Givskov, M., Olsen. L. and Molin, S. (1988) Cloning and expression in Escherichia coli of the gene for extracellular phospholipase A1 from Serratia liquefaciens. J. Bacteriol., 170, 5855–5862.

Jorgensen, R. A. et al, (1979) Mol. Gen. Genet. 177, 65–72.

Kumamoto, C. A. and Nault, A. K. (1989) Characterization of the Escherichia coli protein-export gene secB. Gene, 75 167–175.

Laminet, A. A., Ziegelhoffer, T., Georgopoulos, C and Pl uckthun, A. (1990) The Escherichia coli het shock proteins GroEL and GroES modulate the folding of the β-lactamase precursor. EMBO J., 9, no. 7, 2315–2319.

Lecker, S. H., Lill, R., Ziegelhoffer, T., Georgopoulos, C., Bassford, Jr. P. J., Kumamoto, C. A. and Wickner, W. (1989) Three pure chaperone proteins of Escherichia coli—SecB, trigger factor and GroEL—form soluble complexes with precursor proteins in vitro. EMBO J., 8, no. 9, 2703–2709.

Lecker, S. H., Driessen, A. J. M. and Wickner, W. (1990) ProOmpA contains secondary and tertiary structure prior to translocation and is shielded from aggregation by association with SecB protein. EMBO J., 9, 2309–2314.

Lill, R., Crooke, E., Guthrie, B. and Wickner, W. (1988) The "Trigger Factor Cycle" includes ribosomes, presecretory proteins, and the plasma membrane. Cell, 54, 1013–1018.

Liu, Y. N., Tang, J. L., Clarke, B. R., Dow, J. M. and Daniels, M. J. (1990) A multipurpose broad host range cloning vector and its use to characterise an extracellular protease gene of Xanthomonas campestris pathovar campestris. Mol. Gen. Genet., 222 433–440.

Miyazaki, H., Yanagida, N., Horinouchi, S. and Beppu, T. (1989) Characterization of the Precursor of Serratia marcescens serine protease and COOH-terminal processing of the precursor during its excretion through the outer membrane of Escherichia coli. J. Bacteriol., 6566–6572.

Nakamura, K., Nakamura, A., Takamatsu, H., Yoshikawa, H. and Yamane, K. (1990) Cloning and characterization of a Bacillus subtilis gene homologous to E. coli secY. J. Biochem. 107, 603–607.

Noda, Y., et al. (1990) Molecular cloning of the protocatechuate 4,5-dioxygenase genes of Pseudomonas paucimobilis. J. Bacteriol., 172, 2704–2709.

J. Norrander et al. (1983) Gene 26, 101–106.

Overbeeke, N., Termorshuizen, G. H. M., Giuseppin, M. L. F., Underwood, D. R. and Verrips, C. T. (1990) Secretion of the α-Galactosidase from Cyamopsis tetragonoloba (Guar) by Bacillus subtilis. Appl. and Env. Microbiol., 1429–1434.

Schatz, P. J., Riggs, P. D., Jacq, A., Fath, M. J. and Beckwith, J. (1989) The secE gene encodes an integral membrane protein required for protein export in Escherichia coli. GEN. & DEV., 3 1035–1044.

Schiebel, E., Schwarz, H. and Braun, V. (1989) Subcellular location and unique secretion of the hemolysin of Serratia marcescens. J. of Biol. Chem., 264, no. 27, 16311–16320.

Schmidt, M. G., Rollo, E. E., Grodberg, J. and Oliver, D. B. (1988) Nucleotide sequence of the secA gene and secA (Ts) mutations preventing protein export in Escherichia coli. J. of Bacteriol., 3404–3414.

Suh, J. -W., Boylan, S. A., Thomas, S. M., Dolan, K. M., Oliver, D. B. and Price, C. W. (1990) Isolation of a secY homologue from Bacillus subtilis: evidence for a common protein export pathway in eubacteria. Mol. Microbiol. 4 (2), 305–314.

Watanabe, M. and Blobel, G. (1989) SecB functions as a cytosolic signal recognition factor for protein export in E. coli. Cell. 58, 695–705.

West, S. E. H. and Iglewski, B. H. (1988) Codon usage in Pseudomonas aeruginosa. Nucleic Acids Res., 16, 9323–9335.

Zhu, X., Otha, Y., Jordan, F. and Inouye, M. (1989) Pro-sequence of subtilisin can guide the refolding of denatured subtilisin in an intermolecular process. Nature 339, 483–484.

Zylstra, G. J., Olsean, R. H. and Ballou, D. P. (1989) Genetic organization and sequence of the Pseudomonas cepacia genes for the alfa and beta subunits of protocatechuate 3,4-dioxygenase. J. Bacteriol., 171, 5915–5921.

TABLE 1

Secretion of active lipase production by PG4 cells containing different plasmids on BYPO-Km-Tc plates with or without IPTG

| Plasmid | +IPTG | −IPTG |
| --- | --- | --- |
| pUR6500 (control plasmid) | − | − |
| pUR6502 (tac-lipA + N-term ORF2 genes) | − | − |
| pUR6520 (tac-complete ORF2 gene) | ++ | (+) |
| pUR6522 (tac-lipA/ORF2 genes) | +++ | (+) |

(+) due to the tac promoter not being fully repressed

TABLE 2

The expression and secretion of active lipase in Bacillus subtilis as function of the origin of the signal sequences and the presence of ORF2

| Plasmid | Promoter | Signal sequence | lipA gene | ORF2 gene | Stability construct | Lipase: prod. | Lipase: secr. |
| --- | --- | --- | --- | --- | --- | --- | --- |
| pUR6772 | SPO 2 | − | + | − | + | + | − |
| pUR6743 | SPO 2 | α-amyl | + | − | − | n.d. | n.d. |
| pUR6744 | HPA 2 | pre-prosub | + | − | − | n.d. | n.d. |
| pUR6773 | SPO 2 | glumae | + | − | + | + | − |
| pUR6785 | SPO 2 | glumae | + | + | o | + | + |

TABLE 2-continued

The expression and secretion of active lipase in *Bacillus subtilis* as function of the origin of the signal sequences and the presence of ORF2

| Plasmid | Pro-moter | Signal sequence | lipA gene | ORF2 gene | Stability construct | Lipase: prod. | secr. |
|---------|-----------|-----------------|-----------|-----------|---------------------|---------------|-------| n.d. = not determined
+ = present or stable
o = instable during cultivation
— = not present or construction could not be prepared

LEGENDS TO FIGURES

FIG. 1. Schematic presentation of the construction route of pUR6026, pUR6012 and pUR6200. E=EcoRI, H=HindIII, S=SacII, A=AvaI, BII=BglII, B=BamHI.

FIGS. 2A–J. Nucleotide sequence (SEQ ID NO:9) of a *P. glumae* chromosomal DNA fragment comprising the lipA gene (position 483-ATG to GTG-1556, both underlined) encoding the lipase enzyme (SEQ ID NO:10) and the ORF2 gene (position 1559-ATG to GGT-2617, both overlined).

FIG. 3. Amino acid sequence (SEQ ID NO:11) of the protein encoded by the ORF2 gene as deduced from the nucleotide sequence (SEQ ID NO:12) presented in FIG. 2.

FIG. 4. Schematic representation of the chromosomal situation near the *P. glumae* lipase gene. E=EcoRI, S=SacII, SI=SalI, P=PstI, C=ClaI, M=MluI, B=BamHI.

FIG. 5. Skim milk plate (=LB-agar medium supplemented with 10% skim milk) with colonies of *P. glumae* PG1 (wild type), PG4 and PGT89 (a protease negative Tn5 mutant of PG1, see patent application EP-A-407 225) to determine protease production.

Figure 6:
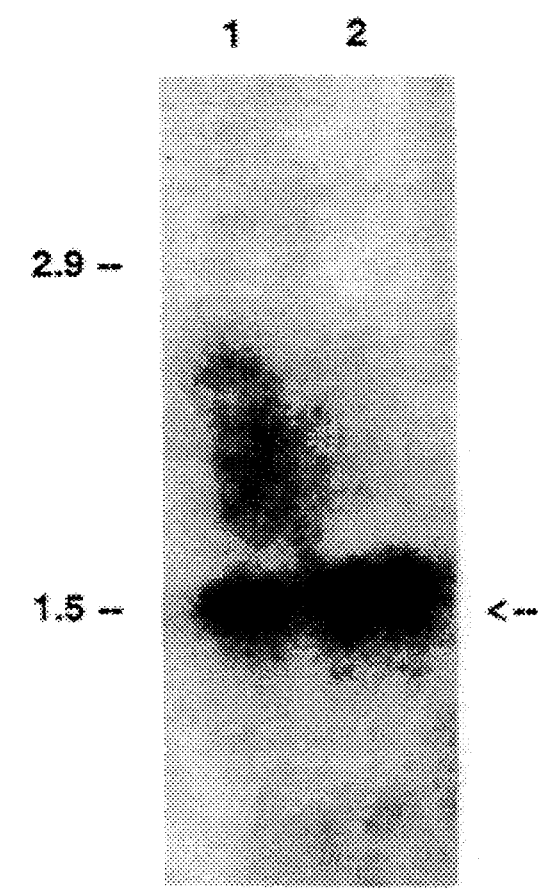

FIG. 6. Northern analysis of *P. glumae* PG1 and PG4; indicated are the 16S (1500 nucleotides) and the 23S (2900 nucleotides) ribosomal RNA. lane 1: PG1, lane 2: PG4

Figure 7:

FIG. 7. BYPO-plate (supplemented with 100 mg/l kanamycin and 0.5 mM IPTG) with *P. glumae* PG4 colonies containing plasmid:
1=pUR6500
2=pUR6502
3=pUR6520
4=pUR6522

FIG. 8. Western analysis of:

| lane 1 | PG1 (pUR6500) cells |
| lane 2 | PG1 (pUR6500) supernatant |
| lane 3 | PG4 (pUR6500) cells |
| lane 4 | PG4 (pUR6500) supernatant |
| lane 5 | mature lipase reference |
| lane 6 | PG4 (pUR6502) supernatant |
| lane 7 | PG4 (pUR6502) cells |
| lane 8 | PG4 (pUR6520) cells |
| lane 9 | PG4 (pUR6520) supernatant |
| lane 10 | PG4 (pUR6522) cells |
| lane 11 | PG4 (pUR6522) supernatant |
| lane 12 | mature lipase reference |

FIG. 9. BYPO-plate (supplemented with 100 mg/l kanamycin and 0.5 mM IPTG) with *P. glumae* colonies.
1=PG1(pUR6500)
2=PG1(pUR6522)
3=PG4(pUR6500)
4=PG4(pUR6522)

FIG. 10. Growth curves of *E. coli* JM109 containing the different plasmid constructs. Overnight cultures of the different strains were prepared in LB-medium supplemented with 25 mg/l kanamycin, and only in the case of *E. coli* JM109 (pUR6518+pUR6520) with 25 mg/l kanamycin and 100 mg/l ampicillin. After diluting the overnight cultures to a OD660 of about 0.15 in 75 ml fresh LB-medium, containing the same antibiotics, the growth was followed in time. After growth for 90 minutes the tac promoter was induced by adding IPTG to a final concentration of 0.2 mM.

FIGS. 11A–11B. Northern analysis of mRNA from *E. coli* strains containing plasmid(s):

| lane 1 | pUR6518 |
| lane 2 | pUR6518 + pUR6520 |
| lane 3 | pUT6522 |
| panel A: | |
| probe = PvuII fragment (position 792 to 1472) | |
| panel B: | |
| probe = NruI fragment (position 1857 to 2526) | |

FIG. 12. Western analysis of *E. coli* strains containing different plasmids. Cells and supernatants were obtained after growing the bacteria under conditions as described in the legend of FIG. 10.

| lane 1 | pUR6518 | cells |
| lane 2 | pUR6522 | " |
| lane 3 | pUR6518 + pUR6520 | " |
| lane 4 | mature lipase reference | |
| lane 5 | pUR6500 | cells |
| lane 6 | empty | |
| lane 7 | pUR6500 | supernatant |
| lane 8 | pUR6518 | " |
| lane 9 | pUR6522 | " |
| lane 10 | pUR6518 + pUR6520 | " |

Figure 13:
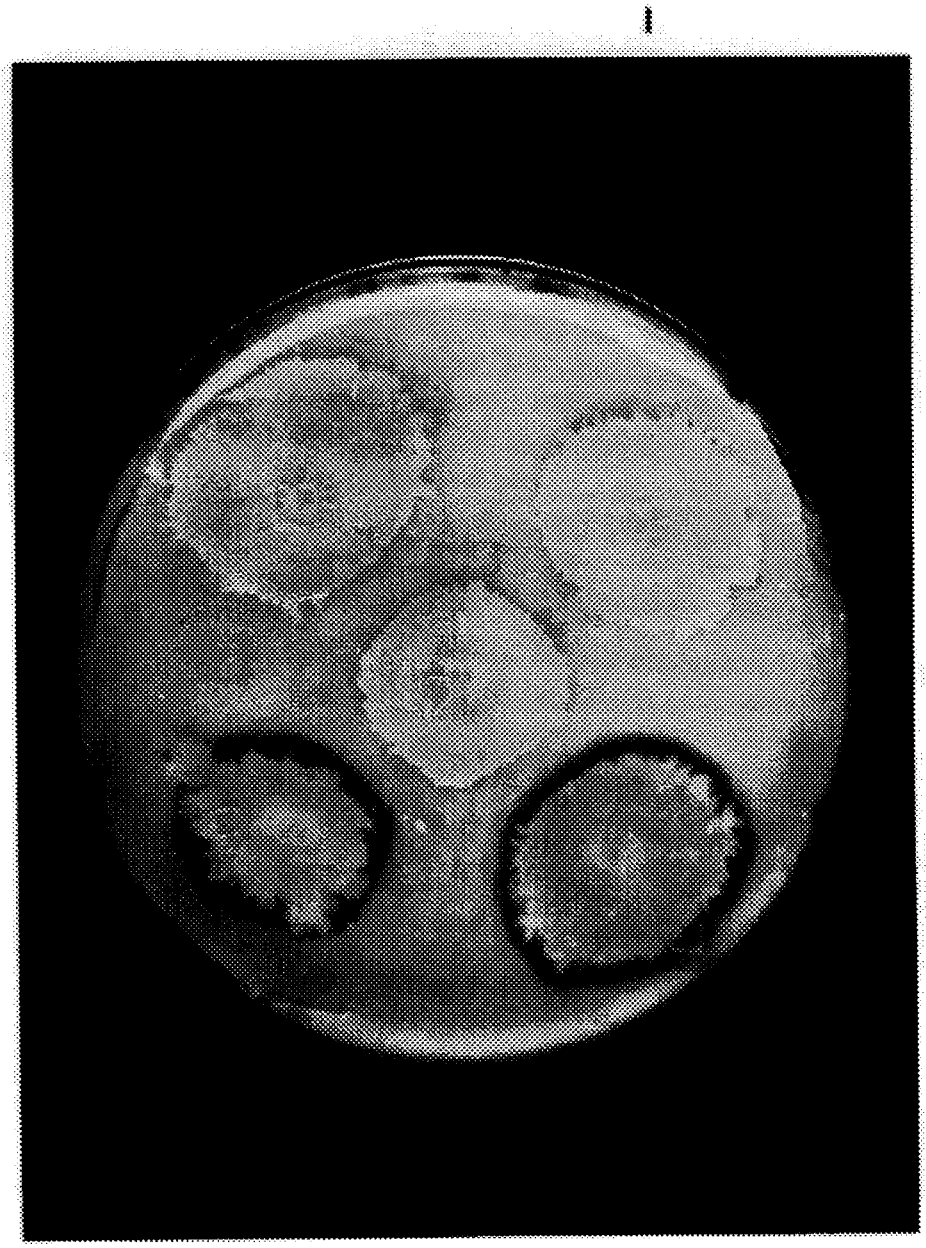

FIG. 13. BYPO-plate (supplemented with 25 mg/l kanamycin) with *B. subtilis* colonies containing plasmid:
1. pUR6772
2. pUR6773
3. pUR6785

Figure 14:
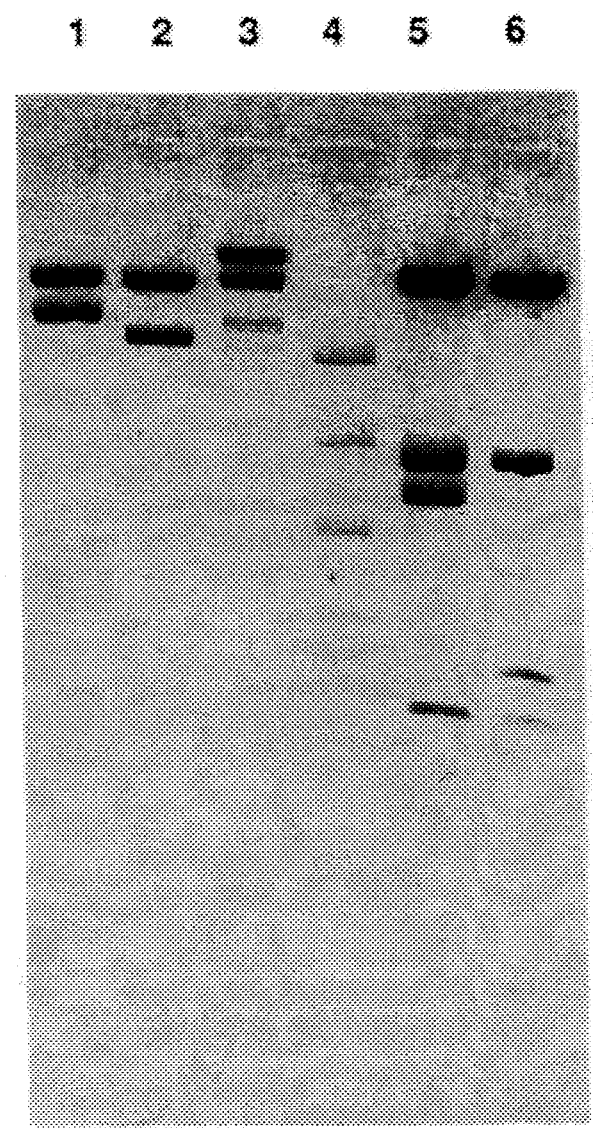

FIG. 14. Restriction enzyme analysis of pUR6785 isolated from a lipase producing *B. subtilis* colonie (lip$^+$) and from a *B. subtilis* colonie which had become lipase negative (lip$^-$).

| lane 1 | lip$^+$ | digested with BstEII and HindIII |
| lane 2 | lip$^-$ | digested with BstEII and HindIII |
| lane 3 | marker A | |
| lane 4 | marker B | |
| lane 5 | lip$^+$ | digested with PstI and BamHI |
| lane 6 | lip$^-$ | digested with PstI and BamHI |

FIGS. 15A–B. Nucleotide sequence (SEQ ID NO:12) of a possible synthetic PstI-BamHI fragment which can be used to replace the corresponding wild type *P. glumae* chromosomal fragment (position ⁻1545 to ⁻2199, containing the DNA stretch having the high G+C content) in constructs encoding the lipA gene and the ORF2 gene from a two gene operon. (The depicted sequence encodes the last 4 amino acids of the lipase and the first 214 amino acids of ORF2.)

FIGS. 16A–B Nucleotide sequence (SEQ ID NO:13) of a possible synthetic EcoRI-BamHI fragment which can be used to replace the 5' part of the wild type *P. glumae* chromosomal ORF2 gene fragment (containing the DNA stretch having the high G+C content) in constructs containing the ORF2 gene after a separate promoter.

We claim:

1. A transformed microorganism which produces lipase, said microorganism being transformed with at least one lipase gene encoding said lipase and at least one gene encoding a lipase-specific stabilization/translocation protein, either one or both of said lipase encoding gene and said lipase-specific stabilization/translocation protein encoding gene originating from *Pseudomonas glumae* PG1.

2. A microorganism according to claim 1, which is selected from the group consisting of
   (a) Gram negative bacteria selected from the group consisting of the species *P. cepacea, P. gladioli, P. glumae, P. mendocina, P. putida* and *P. stutzeri*;
   (b) Gram positive bacteria, and
   (c) eukaryotes.

3. A microorganism according to claim 2, wherein said Gram positive bacteria are selected from the group consisting of members of the family of the genus Bacillus.

4. A microorganism according to claim 2, wherein said eukaryotes are selected from the group consisting of members of the yeast genera Hansenula, Kluyveromyces, Pichia, Saccharomyces, and the mould genus Aspergillus, and other lower eukaryotes.

5. A microorganism according to claim 1, in which the lipase or its gene originates from *Pseudomonas glumae* PG1.

6. A microorganism according to claim 1, in which the lipase shows immunological cross reactivity with an antiserum raised against a lipase from *Chromobacter viscosum* var *lipolyticum* NRRL B-3673, or against a lipase from Alcaligenes PL-679, ATCC 31371 or FERM-P 3783, or against a lipase from *Pseudomonas fluorescens* IAM 1057.

7. An isolated nucleotide sequence encoding a lipase-specific stabilization/translocation protein as given in FIG. 3.

8. A sequence as claimed in claim 7, in which the first about 200 codons of that nucleotide sequence encode essentially the same amino acids, but have an altered G+C content such that said altered G+C content is equal to that of messenger RNAs translated in a host cell into which said sequence is inserted and translated.

9. A sequence as claimed in claim 7, which has a G+C content and codon usage essentially equal to the G+C content and codon usage of messenger RNAs translated in a host cell into which said sequence is inserted and translated.

10. A process for producing a lipase by a transformed microorganism, whereby a microorganism according to claim 1 is cultivated under conditions and in a medium whereby the lipase is produced and secreted, and subsequently the lipase is collected from the medium.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AATTCTGCAG TGGCAGACAC GCGTA    25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AGCTTACGCG TGTCTGCCAC TGCAG    25

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AATTTGGTAA CCGGATCAGA AAGGAGGTGA TCGAATTCAA    40

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AGCTTTGAAT TCGATCACCT CCTTTCTGAT CCGGTTACCA    40

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CGTGGAGCAG GAGGTTAGTG ACTGCAGTTA CTA    33

( 2 ) INFORMATION FOR SEQ ID NO:6:

( i ) SEQUENCE CHARACTERISTICS:
        ( A ) LENGTH: 39 base pairs (B) TYPE: nucleic acid
(C) STRANDEDNESS: single
(D) TOPOLOGY: linear (xi) SEQUENCE DESCRIPTION: SEQ ID NO:6:

AGCTTAGTAA CTGCAGTCAC TAACCTCCTG CTCCACGAT    39

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:7:

AATTCATGGC GCAGGCCGAT    20

(2) INFORMATION FOR SEQ ID NO:8:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:8:

CGGCCTGCGC CATG    14

(2) INFORMATION FOR SEQ ID NO:9:

(i) SEQUENCE CHARACTERISTICS:
(A) LENGTH: 2900 base pairs
(B) TYPE: nucleic acid
(C) STRANDEDNESS: double
(D) TOPOLOGY: linear (ix) FEATURE:
(A) NAME/KEY: CDS
(B) LOCATION: 483..1556

(ix) FEATURE:
(A) NAME/KEY: CDS
(B) LOCATION: 1559..2617

(xi) SEQUENCE DESCRIPTION: SEQ ID NO:9:

```
GGATCCTGCC TTGAGCCCGG GCGCGTCCCG GACGCGCTTC CGGGTTCATC CCCGACCCGT      60
TCTGAATTCA CCTTGAACGC AGGCGTTTCG CGCGCGGCGG CCTTCGCGCT GCGCCGCAAT     120
ACGTCTCGCG CCGTGTCATG TCGATTCGCG ATGCAATCGT CGGCAATCGG CGTGATTGTT     180
GCGCCCGCAA CCTGATCGCC GCCCGCGCCC GCGTGGCGCG CGCGCGGCAC GCCATTCACC     240
GGATCGATCG CGCCCGCTTG CGCGCCGCAG CATCCGCGCC GTCATATGTC CACCCGCCGC     300
GCGCGGCGCT GTCCATCGAG TAGAGACGCC TATCCAAACG GCCGTCTGAT TGCAGACAGG     360
AGCCGCGCCG CCATGTTTCA CTCCGCACTT GCCGCTCGAG CGTGCCCGAC GACCTGAGAA     420
CGGCGCGGCG CCGCGCGGCG TGGCATTCCG GATCGACGTA ACCGATAACG ATGGAGATAA     480
AC ATG GTC AGA TCG ATG CGT TCC AGG GTG GCG GCG AGG GCG GTG GCA        527
   Met Val Arg Ser Met Arg Ser Arg Val Ala Ala Arg Ala Val Ala
   1               5                  10                  15
TGG GCG TTG GCG GTG ATG CCG CTG GCC GGC GCG GCC GGG TTG ACG ATG      575
Trp Ala Leu Ala Val Met Pro Leu Ala Gly Ala Ala Gly Leu Thr Met
           20                  25                  30
```

```
GCC GCG TCG CCC GCG GCC GTC GCG GCG GAC ACC TAC GCG GCG ACG CGC     623
Ala Ala Ser Pro Ala Ala Val Ala Ala Asp Thr Tyr Ala Ala Thr Arg
            35                  40                  45

TAT CCG GTG ATC CTC GTC CAC GGC CTC GCG GGC ACC GAC AAG TTC GCG     671
Tyr Pro Val Ile Leu Val His Gly Leu Ala Gly Thr Asp Lys Phe Ala
        50                  55                  60

AAC GTG GTG GAC TAT TGG TAC GGA ATC CAG AGC GAT CTG CAA TCG CAT     719
Asn Val Val Asp Tyr Trp Tyr Gly Ile Gln Ser Asp Leu Gln Ser His
    65                  70                  75

GGC GCG AAG GTG TAC GTC GCG AAT CTC TCG GGA TTC CAG AGC GAC GAC     767
Gly Ala Lys Val Tyr Val Ala Asn Leu Ser Gly Phe Gln Ser Asp Asp
80                  85                  90                  95

GGG CCG AAC GGC CGC GGC GAG CAG CTG CTC GCC TAC GTG AAG CAG GTG     815
Gly Pro Asn Gly Arg Gly Glu Gln Leu Leu Ala Tyr Val Lys Gln Val
                100                 105                 110

CTC GCG GCC ACC GGC GCG ACC AAG GTG AAC CTG ATC GGC CAC AGC CAG     863
Leu Ala Ala Thr Gly Ala Thr Lys Val Asn Leu Ile Gly His Ser Gln
            115                 120                 125

GGC GGC CTG ACC TCG CGC TAC GTC GCG GCC GTC GCG CCG CAA CTG GTG     911
Gly Gly Leu Thr Ser Arg Tyr Val Ala Ala Val Ala Pro Gln Leu Val
        130                 135                 140

GCC TCG GTG ACG ACG ATC GGC ACG CCG CAT CGC GGC TCC GAG TTC GCC     959
Ala Ser Val Thr Thr Ile Gly Thr Pro His Arg Gly Ser Glu Phe Ala
    145                 150                 155

GAC TTC GTG CAG GAC GTG CTG AAG ACC GAT CCG ACC GGG CTC TCG TCG     1007
Asp Phe Val Gln Asp Val Leu Lys Thr Asp Pro Thr Gly Leu Ser Ser
160                 165                 170                 175

ACG GTG ATC GCC GCC TTC GTC AAC GTG TTC GGC ACG CTC GTC AGC AGC     1055
Thr Val Ile Ala Ala Phe Val Asn Val Phe Gly Thr Leu Val Ser Ser
                180                 185                 190

TCG CAC AAC ACC GAC CAG GAC GCG CTC GCG GCG CTG CGC ACG CTC ACC     1103
Ser His Asn Thr Asp Gln Asp Ala Leu Ala Ala Leu Arg Thr Leu Thr
            195                 200                 205

ACC GCG CAG ACC GCC ACC TAC AAC CGG AAC TTC CCG AGC GCG GGC CTG     1151
Thr Ala Gln Thr Ala Thr Tyr Asn Arg Asn Phe Pro Ser Ala Gly Leu
        210                 215                 220

GGC GCG CCC GGT TCG TGC CAG ACG GGC GCC GCG ACC GAA ACC GTC GGC     1199
Gly Ala Pro Gly Ser Cys Gln Thr Gly Ala Ala Thr Glu Thr Val Gly
    225                 230                 235

GGC AGC CAG CAC CTG CTC TAT TCG TGG GGC GGC ACC GCG ATC CAG CCC     1247
Gly Ser Gln His Leu Leu Tyr Ser Trp Gly Gly Thr Ala Ile Gln Pro
240                 245                 250                 255

ACC TCC ACC GTG CTC GGC GTG ACC GGC GCG ACC GAC ACC AGC ACC GGC     1295
Thr Ser Thr Val Leu Gly Val Thr Gly Ala Thr Asp Thr Ser Thr Gly
                260                 265                 270

ACG CTC GAC GTC GCG AAC GTG ACC GAC CCG TCC ACG CTC GCG CTG CTC     1343
Thr Leu Asp Val Ala Asn Val Thr Asp Pro Ser Thr Leu Ala Leu Leu
            275                 280                 285

GCC ACC GGC GCG GTG ATG ATC AAT CGC GCC TCG GGG CAG AAC GAC GGG     1391
Ala Thr Gly Ala Val Met Ile Asn Arg Ala Ser Gly Gln Asn Asp Gly
        290                 295                 300

CTC GTC TCG CGC TGC AGC TCG CTG TTC GGG CAG GTG ATC AGC ACC AGC     1439
Leu Val Ser Arg Cys Ser Ser Leu Phe Gly Gln Val Ile Ser Thr Ser
    305                 310                 315

TAC CAC TGG AAC CAT CTC GAC GAG ATC AAC CAG CTG CTC GGC GTG CGC     1487
Tyr His Trp Asn His Leu Asp Glu Ile Asn Gln Leu Leu Gly Val Arg
320                 325                 330                 335

GGC GCC AAC GCG GAA GAT CCG GTC GCG GTG ATC CGC ACG CAC GTG AAC     1535
Gly Ala Asn Ala Glu Asp Pro Val Ala Val Ile Arg Thr His Val Asn
                340                 345                 350
```

| | | | | | | | | | | | | | | | | |
|---|---|---|---|---|---|---|---|---|---|---|---|---|---|---|---|---|
| CGG | CTC | AAG | CTG | CAG | GGC | GTG | TG | ATG | GCG | CAG | GCC | GAT | CGT | CCG | GCG | 1582 |
| Arg | Leu | Lys | Leu 355 | Gln | Gly | Val | | Met 1 | Ala | Gln | Ala | Asp 5 | Arg | Pro | Ala | |
| CGC | GGC | GGG | CTG | GCC | GCG | CGC | CCG | ATG | CGC | GGC | GCG | TCG | TTC | GCG | CTG | 1630 |
| Arg | Gly 10 | Gly | Leu | Ala | Ala | Arg | Pro | Met 15 | Arg | Gly | Ala | Ser | Phe 20 | Ala | Leu | |
| GCC | GGG | CTC | GTC | GCG | TGT | GCC | GCC | TGT | GCC | GCG | GTC | GTG | CTG | TGG | CTT | 1678 |
| Ala 25 | Gly | Leu | Val | Ala | Cys 30 | Ala | Ala | Cys | Ala | Ala 35 | Val | Val | Leu | Trp | Leu 40 | |
| CGG | CCC | GCC | GCC | CCG | TCG | CCC | GCG | CCG | GCC | GGC | GCC | GTC | GCG | GGC | GGG | 1726 |
| Arg | Pro | Ala | Ala | Pro 45 | Ser | Pro | Ala | Pro | Ala 50 | Gly | Ala | Val | Ala | Gly 55 | Gly | |
| CCG | GCG | GCC | GGC | GTG | CCC | GCC | GCG | GCA | AGC | GGC | GCG | GCG | GAG | GCC | GCC | 1774 |
| Pro | Ala | Ala | Gly 60 | Val | Pro | Ala | Ala | Ala 65 | Ser | Gly | Ala | Ala | Glu 70 | Ala | Ala | |
| ATG | CCG | TTG | CCG | GCG | GCG | CTG | CCG | GGC | GCG | CTG | GCT | GGC | TCG | CAT | GCG | 1822 |
| Met | Pro | Leu 75 | Pro | Ala | Ala | Leu | Pro 80 | Gly | Ala | Leu | Ala | Gly 85 | Ser | His | Ala | |
| CCG | CGC | CTG | CCG | CTG | GCC | GCC | GGC | GGC | CGG | CTC | GCG | AGG | ACG | CGC | GCG | 1870 |
| Pro | Arg 90 | Leu | Pro | Leu | Ala | Ala 95 | Gly | Gly | Arg | Leu | Ala 100 | Arg | Thr | Arg | Ala | |
| GTG | CGC | GAG | TTC | TTC | GAC | TAT | TGC | CTG | ACC | GCG | CAG | GGC | GAA | CTG | ACG | 1918 |
| Val 105 | Arg | Glu | Phe | Phe | Asp 110 | Tyr | Cys | Leu | Thr | Ala 115 | Gln | Gly | Glu | Leu | Thr 120 | |
| CCC | GCC | GCG | CTC | GAT | GCG | CTG | GTG | CGG | CGC | GAG | ATC | GCC | GCG | CAG | CTT | 1966 |
| Pro | Ala | Ala | Leu | Asp 125 | Ala | Leu | Val | Arg | Arg 130 | Glu | Ile | Ala | Ala | Gln 135 | Leu | |
| GAC | GGC | AGC | CCC | GCG | CAA | GCG | GAG | GCG | CTC | GGC | GTC | TGG | CGC | CGC | TAT | 2014 |
| Asp | Gly | Ser | Pro 140 | Ala | Gln | Ala | Glu | Ala 145 | Leu | Gly | Val | Trp | Arg 150 | Arg | Tyr | |
| CGC | GCC | TAC | TTC | GAC | GCG | CTC | GCG | CAA | TTG | CCC | GGC | GAC | GGC | GCG | GTG | 2062 |
| Arg | Ala | Tyr 155 | Phe | Asp | Ala | Leu | Ala 160 | Gln | Leu | Pro | Gly | Asp 165 | Gly | Ala | Val | |
| CTC | GGC | GAC | AAG | CTC | GAT | CCG | GCC | GCC | ATG | CAG | CTC | GCG | CTC | GAT | CAG | 2110 |
| Leu | Gly 170 | Asp | Lys | Leu | Asp | Pro 175 | Ala | Ala | Met | Gln | Leu 180 | Ala | Leu | Asp | Gln | |
| CGC | GCG | GCG | CTG | GCC | GAC | CGC | ACG | CTC | GGC | GAG | TGG | GCC | GAG | CCG | TTC | 2158 |
| Arg | Ala 185 | Ala | Leu | Ala | Asp 190 | Arg | Thr | Leu | Gly | Glu 195 | Trp | Ala | Glu | Pro | Phe 200 | |
| TTC | GGC | GAC | GAG | CAG | CGC | CGG | CAG | CGC | CAT | GAC | CTC | GAA | CGG | ATC | CGG | 2206 |
| Phe | Gly | Asp | Glu | Gln 205 | Arg | Arg | Gln | Arg | His 210 | Asp | Leu | Glu | Arg | Ile 215 | Arg | |
| ATC | GCC | AAC | GAC | ACC | ACG | CTG | AGC | CCT | GAG | CAG | AAG | GCC | GCG | CGG | CTT | 2254 |
| Ile | Ala | Asn | Asp 220 | Thr | Thr | Leu | Ser | Pro 225 | Glu | Gln | Lys | Ala | Ala 230 | Arg | Leu | |
| GCC | GCG | CTC | GAC | GCG | CAG | CTG | ACG | CCG | GAC | GAG | CGC | GCG | CAG | CAG | GCG | 2302 |
| Ala | Ala | Leu 235 | Asp | Ala | Gln | Leu | Thr 240 | Pro | Asp | Glu | Arg | Ala 245 | Gln | Gln | Ala | |
| GCG | CTG | CAT | GCG | CAG | CAG | GAC | GCG | GTG | ACG | AAG | ATC | GCC | GAC | TTG | CAG | 2350 |
| Ala | Leu | His | Ala | Gln 250 | Gln | Asp | Ala | Val | Thr 255 | Lys | Ile | Ala | Asp | Leu 260 | Gln | |
| AAG | GCC | GGC | GCG | ACG | CCC | GAC | CAG | ATG | CGC | GCG | CAG | ATC | GCG | CAG | ACG | 2398 |
| Lys 265 | Ala | Gly | Ala | Thr | Pro 270 | Asp | Gln | Met | Arg | Ala 275 | Gln | Ile | Ala | Gln | Thr 280 | |
| CTC | GGG | CCC | GAG | GCG | GCC | GCG | CGC | GCC | GCG | CAG | ATG | CAG | CAG | GAC | GAC | 2446 |
| Leu | Gly | Pro | Glu | Ala 285 | Ala | Ala | Arg | Ala | Ala 290 | Gln | Met | Gln | Gln | Asp 295 | Asp | |
| GAG | GCG | TGG | CAG | ACG | CGC | TAT | CAA | GCC | TAT | GCG | GCC | GAG | CGC | GAC | CGG | 2494 |
| Glu | Ala | Trp | Gln | Thr 300 | Arg | Tyr | Gln | Ala | Tyr 305 | Ala | Ala | Glu | Arg | Asp 310 | Arg | |

```
ATC GCG GCG CAG GGG CTC GCG CCG CAG GAT CGC GAT GCG CGG ATC GCG      2542
Ile Ala Ala Gln Gly Leu Ala Pro Gln Asp Arg Asp Ala Arg Ile Ala
        315                 320                 325

CAG CTC AGG CAG CAG ACT TTC ACG GCG CCG GGG GAG GCG ATC CGC GCG      2590
Gln Leu Arg Gln Gln Thr Phe Thr Ala Pro Gly Glu Ala Ile Arg Ala
330                 335                 340

GCG TCG CTC GAT CGC GGC GCG GGC GGT TAGGGGCGC CGGCGTGCCG             2637
Ala Ser Leu Asp Arg Gly Ala Gly Gly
345                 350

GGCACCGTGT GCTTCGCGAG TGCTTCGAAC GGGTGGGGCC GCACGGCGTT TCCAGCCGCT    2697

GCATCGCGTG TTTCGTACTG AAATGGCATG AGTGACAGCG TGCCGACAGC GTGCTGACAG    2757

GGTTCCCGGT TTTTGCCTTT CCACGTGCTT TCATTGGCGC CGCGAGCGAG CAAGAATCAC    2817

GACGCTCTGC AACAATGCGG GGCGATGGCG CGTTTGACGG TCGGAATCGA TGCAAACGCG    2877

CCGCCGCGTC GTTCCATCCG CGG                                            2900
```

( 2 ) INFORMATION FOR SEQ ID NO:10:

( i ) SEQUENCE CHARACTERISTICS:
        ( A ) LENGTH: 358 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Val Arg Ser Met Arg Ser Arg Val Ala Arg Ala Val Ala Trp
  1               5                  10                  15

Ala Leu Ala Val Met Pro Leu Ala Gly Ala Ala Gly Leu Thr Met Ala
                 20                  25                  30

Ala Ser Pro Ala Ala Val Ala Ala Asp Thr Tyr Ala Ala Thr Arg Tyr
             35                  40                  45

Pro Val Ile Leu Val His Gly Leu Ala Gly Thr Asp Lys Phe Ala Asn
         50                  55                  60

Val Val Asp Tyr Trp Tyr Gly Ile Gln Ser Asp Leu Gln Ser His Gly
 65                  70                  75                  80

Ala Lys Val Tyr Val Ala Asn Leu Ser Gly Phe Gln Ser Asp Asp Gly
                 85                  90                  95

Pro Asn Gly Arg Gly Glu Gln Leu Leu Ala Tyr Val Lys Gln Val Leu
                100                 105                 110

Ala Ala Thr Gly Ala Thr Lys Val Asn Leu Ile Gly His Ser Gln Gly
            115                 120                 125

Gly Leu Thr Ser Arg Tyr Val Ala Ala Val Ala Pro Gln Leu Val Ala
        130                 135                 140

Ser Val Thr Thr Ile Gly Thr Pro His Arg Gly Ser Glu Phe Ala Asp
145                 150                 155                 160

Phe Val Gln Asp Val Leu Lys Thr Asp Pro Thr Gly Leu Ser Ser Thr
                165                 170                 175

Val Ile Ala Ala Phe Val Asn Val Phe Gly Thr Leu Val Ser Ser Ser
            180                 185                 190

His Asn Thr Asp Gln Asp Ala Leu Ala Ala Leu Arg Thr Leu Thr Thr
        195                 200                 205

Ala Gln Thr Ala Thr Tyr Asn Arg Asn Phe Pro Ser Ala Gly Leu Gly
    210                 215                 220

Ala Pro Gly Ser Cys Gln Thr Gly Ala Ala Thr Glu Thr Val Gly Gly
225                 230                 235                 240
```

```
Ser  Gln  His  Leu  Leu  Tyr  Ser  Trp  Gly  Gly  Thr  Ala  Ile  Gln  Pro  Thr
               245                250                     255

Ser  Thr  Val  Leu  Gly  Val  Thr  Gly  Ala  Thr  Asp  Thr  Ser  Thr  Gly  Thr
               260                265                     270

Leu  Asp  Val  Ala  Asn  Val  Thr  Asp  Pro  Ser  Thr  Leu  Ala  Leu  Leu  Ala
               275                280                     285

Thr  Gly  Ala  Val  Met  Ile  Asn  Arg  Ala  Ser  Gly  Gln  Asn  Asp  Gly  Leu
               290                295                     300

Val  Ser  Arg  Cys  Ser  Ser  Leu  Phe  Gly  Gln  Val  Ile  Ser  Thr  Ser  Tyr
305                      310                315                          320

His  Trp  Asn  His  Leu  Asp  Glu  Ile  Asn  Gln  Leu  Leu  Gly  Val  Arg  Gly
               325                330                     335

Ala  Asn  Ala  Glu  Asp  Pro  Val  Ala  Val  Ile  Arg  Thr  His  Val  Asn  Arg
               340                345                     350

Leu  Lys  Leu  Gln  Gly  Val
               355
```

( 2 ) INFORMATION FOR SEQ ID NO:11:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Ala  Gln  Ala  Asp  Arg  Pro  Ala  Arg  Gly  Gly  Leu  Ala  Ala  Arg  Pro
1                        5                 10                          15

Met  Arg  Gly  Ala  Ser  Phe  Ala  Leu  Ala  Gly  Leu  Val  Ala  Cys  Ala  Ala
               20                 25                     30

Cys  Ala  Ala  Val  Val  Leu  Trp  Leu  Arg  Pro  Ala  Ala  Pro  Ser  Pro  Ala
               35                 40                     45

Pro  Ala  Gly  Ala  Val  Ala  Gly  Gly  Pro  Ala  Ala  Gly  Val  Pro  Ala  Ala
               50                 55                     60

Ala  Ser  Gly  Ala  Ala  Glu  Ala  Ala  Met  Pro  Leu  Pro  Ala  Ala  Leu  Pro
65                      70                 75                            80

Gly  Ala  Leu  Ala  Gly  Ser  His  Ala  Pro  Arg  Leu  Pro  Leu  Ala  Ala  Gly
               85                 90                     95

Gly  Arg  Leu  Ala  Arg  Thr  Arg  Ala  Val  Arg  Glu  Phe  Phe  Asp  Tyr  Cys
               100                105                    110

Leu  Thr  Ala  Gln  Gly  Glu  Leu  Thr  Pro  Ala  Ala  Leu  Asp  Ala  Leu  Val
               115                120                    125

Arg  Arg  Glu  Ile  Ala  Ala  Gln  Leu  Asp  Gly  Ser  Pro  Ala  Gln  Ala  Glu
130                     135                140

Ala  Leu  Gly  Val  Trp  Arg  Arg  Tyr  Arg  Ala  Tyr  Phe  Asp  Ala  Leu  Ala
145                     150                155                           160

Gln  Leu  Pro  Gly  Asp  Gly  Ala  Val  Leu  Gly  Asp  Lys  Leu  Asp  Pro  Ala
               165                170                    175

Ala  Met  Gln  Leu  Ala  Leu  Asp  Gln  Arg  Ala  Ala  Leu  Ala  Asp  Arg  Thr
               180                185                    190

Leu  Gly  Glu  Trp  Ala  Glu  Pro  Phe  Phe  Gly  Asp  Glu  Gln  Arg  Arg  Gln
               195                200                    205

Arg  His  Asp  Leu  Glu  Arg  Ile  Arg  Ile  Ala  Asn  Asp  Thr  Thr  Leu  Ser
               210                215                    220

Pro  Glu  Gln  Lys  Ala  Ala  Arg  Leu  Ala  Ala  Leu  Asp  Ala  Gln  Leu  Thr
225                     230                235                           240
```

| Pro | Asp | Glu | Arg | Ala | Gln | Gln | Ala | Ala | Leu | His | Ala | Gln | Gln | Asp | Ala |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Val | Thr | Lys | Ile | Ala | Asp | Leu | Gln | Lys | Ala | Gly | Ala | Thr | Pro | Asp | Gln |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Met | Arg | Ala | Gln | Ile | Ala | Gln | Thr | Leu | Gly | Pro | Glu | Ala | Ala | Ala | Arg |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ala | Ala | Gln | Met | Gln | Gln | Asp | Asp | Glu | Ala | Trp | Gln | Thr | Arg | Tyr | Gln |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Ala | Tyr | Ala | Ala | Glu | Arg | Asp | Arg | Ile | Ala | Ala | Gln | Gly | Leu | Ala | Pro |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Gln | Asp | Arg | Asp | Ala | Arg | Ile | Ala | Gln | Leu | Arg | Gln | Gln | Thr | Phe | Thr |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Ala | Pro | Gly | Glu | Ala | Ile | Arg | Ala | Ala | Ser | Leu | Asp | Arg | Gly | Ala | Gly |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

Gly ( 2 ) INFORMATION FOR SEQ ID NO:12:

( i ) SEQUENCE CHARACTERISTICS:
        ( A ) LENGTH: 660 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:12:

| CTGCAGGGCG | TGTGATGGCG | CAGGCCGATC | GTCCTGCAAG | AGGAGGCCTG | GCTGCAAGAC | 60 |
| CTATGAGAGG | CGCATCTTTC | GCGCTGGCAG | GTCTGGTCGC | GTGTGCAGCT | TGTGCAGCCG | 120 |
| TAGTACTGTG | GCTGAGACCA | GCGGCACCTT | CTCCTGCTCC | AGCAGGCGCA | GTTGCAGGCG | 180 |
| GACCTGCCGC | GGGAGTTCCA | GCGGCAGCAT | CTGGCGCAGC | TGAAGCAGCG | ATGCCTTTAC | 240 |
| CTGCTGCATT | GCCTGGCGCA | CTTGCCGGAT | CGCATGCGCC | AAGACTGCCG | CTTGCGGCAG | 300 |
| GTGGACGCTT | GGCACGCACA | AGAGCCGTCA | GAGAGTTCTT | TGATTATTGC | CTTACTGCGC | 360 |
| AGGGCGAATT | GACGCCTGCT | GCCCTGGACG | CACTGGTTAG | ACGCGAAATT | GCAGCGCAAC | 420 |
| TTGATGGATC | TCCAGCTCAA | GCAGAAGCTC | TTGGCGTCTG | GCGTAGATAT | CGCGCGTACT | 480 |
| TTGATGCATT | GGCCCAGCTT | CCTGGCGACG | GAGCGGTTCT | TGGTGATAAA | TTAGATCCTG | 540 |
| CCGCTATGCA | ACTGGCACTT | GATCAACGTG | CAGCGTTGGC | CGACCGCACG | CTTGGCGAGT | 600 |
| GGGCTGAACC | ATTCTTTGGC | GACGAGCAGA | GAAGACAACG | CCATGATCTT | GAAAGGATCC | 660 |

( 2 ) INFORMATION FOR SEQ ID NO:13:

( i ) SEQUENCE CHARACTERISTICS:
        ( A ) LENGTH: 652 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:13:

| GAATTCATGG | CGCAGGCCGA | TCGTCCTGCA | AGAGGAGGCC | TGGCTGCAAG | ACCTATGAGA | 60 |
| GGCGCATCTT | TCGCGCTGGC | AGGTCTGGTC | GCGTGTGCAG | CTTGTGCAGC | CGTAGTACTG | 120 |
| TGGCTGAGAC | CAGCGGCACC | TTCTCCTGCT | CCAGCAGGCG | CAGTTGCAGG | CGGACCTGCC | 180 |
| GCGGGAGTTC | CAGCGGCAGC | ATCTGGCGCA | GCTGAAGCAG | CGATGCCTTT | ACCTGCTGCA | 240 |
| TTGCCTGGCG | CACTTGCCGG | ATCGCATGCG | CCAAGACTGC | CGCTTGCGGC | AGGTGGACGC | 300 |
| TTGGCACGCA | CAAGAGCCGT | CAGAGAGTTC | TTTGATTATT | GCCTTACTGC | GCAGGGCGAA | 360 |

| | | | | | |
|---|---|---|---|---|---|
| TTGACGCCTG | CTGCCCTGGA | CGCACTGGTT | AGACGCGAAA | TTGCAGCGCA | ACTTGATGGA | 420 |
| TCTCCAGCTC | AAGCAGAAGC | TCTTGGCGTC | TGGCGTAGAT | ATCGCGCGTA | CTTTGATGCA | 480 |
| TTGGCCCAGC | TTCCTGGCGA | CGGAGCGGTT | CTTGGTGATA | AATTAGATCC | TGCCGCTATG | 540 |
| CAACTGGCAC | TTGATCAACG | TGCAGCGTTG | GCCGACCGCA | CGCTTGGCGA | GTGGGCTGAA | 600 |
| CCATTCTTTG | GCGACGAGCA | GAGAAGACAA | CGCCATGATC | TTGAAAGGAT | CC | 652 |